US012616972B2

(12) United States Patent
Facer et al.

(10) Patent No.: US 12,616,972 B2
(45) Date of Patent: May 5, 2026

(54) MAGNETIC PARTICLE ISOLATION DEVICE AND METHODS OF USE

(71) Applicant: LevitasBio, Inc., San Francisco, CA (US)

(72) Inventors: Geoffrey Facer, Redwood City, CA (US); Kevin Travers, Menlo Park, CA (US); Andreja Jovic, Sunnyvale, CA (US); Theodorus Evan De Groot, Oakland, CA (US)

(73) Assignee: LEVITASBIO, INC., Menlo Park, CA (US)

( * ) Notice: Subject to any disclaimer, the term of this patent is extended or adjusted under 35 U.S.C. 154(b) by 821 days.

(21) Appl. No.: 17/033,345

(22) Filed: Sep. 25, 2020

(65) Prior Publication Data

US 2021/0260577 A1    Aug. 26, 2021

Related U.S. Application Data

(63) Continuation of application No. PCT/US2019/024138, filed on Mar. 26, 2019.
(Continued)

(51) Int. Cl.
*B01L 3/00* (2006.01)
*B03C 1/033* (2006.01)
(Continued)

(52) U.S. Cl.
CPC ..... *B01L 3/50273* (2013.01); *B01L 3/502761* (2013.01); *B03C 1/0332* (2013.01);
(Continued)

(58) Field of Classification Search
CPC ........... B01L 3/50273; B01L 3/502761; B01L 2200/0652; B01L 2300/0816;
(Continued)

(56) References Cited

U.S. PATENT DOCUMENTS 5,980,479 A    11/1999  Kutushov
8,689,981 B2    4/2014  Stone et al.
(Continued)

FOREIGN PATENT DOCUMENTS

CN          1650162 A        8/2005
CN          1899698 A        1/2007
(Continued)

OTHER PUBLICATIONS

What is Ferrofluid. ferrofluid. (2024). https://ferrofluid.com/ (Year: 2024).*
(Continued)

*Primary Examiner* — Elizabeth A Robinson
*Assistant Examiner* — Tingchen Shi
(74) *Attorney, Agent, or Firm* — WILSON SONSINI GOODRICH & ROSATI

(57) ABSTRACT

The present invention provides for devices and methods of isolating particles. A fluidics particle isolation device is disclosed having a fluidic channel extending therethrough, wherein a segment of the fluidic channel is exposed to an asymmetric magnetic field such that when a solution containing the particles in a paramagnetic medium are passed through the magnetic field, the particles are isolated within the solution.

18 Claims, 17 Drawing Sheets

Related U.S. Application Data

(60) Provisional application No. 62/728,684, filed on Sep. 7, 2018, provisional application No. 62/648,300, filed on Mar. 26, 2018.

(51) Int. Cl.
    *B03C 1/28*          (2006.01)
    *C12M 1/00*          (2006.01)

(52) U.S. Cl.
    CPC ............ *B03C 1/0335* (2013.01); *B03C 1/288* (2013.01); *C12M 47/04* (2013.01); *B01L 2200/0652* (2013.01); *B01L 2300/0816* (2013.01); *B01L 2300/0864* (2013.01); *B01L 2400/0406* (2013.01); *B01L 2400/043* (2013.01); *B03C 2201/18* (2013.01)

(58) Field of Classification Search
    CPC ..... B01L 2300/0864; B01L 2400/0406; B01L 2400/043; B03C 2201/18; B03C 1/0332; B03C 1/0335; B03C 1/288; C12M 47/04
    See application file for complete search history.

(56)             References Cited

U.S. PATENT DOCUMENTS

| | | | |
|---|---|---|---|
| 9,873,126 | B2 | 1/2018 | Mao et al. |
| 2004/0009614 | A1 | 1/2004 | Ahn et al. |
| 2009/0047297 | A1 | 2/2009 | Kim et al. |
| 2012/0080360 | A1 | 4/2012 | Stone et al. |
| 2014/0370519 | A1 | 12/2014 | Vangbo et al. |
| 2016/0244714 | A1 | 8/2016 | Spuhler et al. |
| 2016/0370386 | A1 | 12/2016 | Demirci et al. |
| 2017/0333914 | A1 | 11/2017 | Kang et al. |
| 2018/0001324 | A1 | 1/2018 | Khashan |

FOREIGN PATENT DOCUMENTS

| | | |
|---|---|---|
| CN | 206325691 U | 7/2017 |
| WO | WO-2010117458 A1 | 10/2010 |
| WO | WO-2017059353 A1 * | 4/2017 ........ B01L 3/502761 |
| WO | WO-2019191137 A1 | 10/2019 |

OTHER PUBLICATIONS

CN201980035906.8 Office Action dated Jan. 18, 2023 (w/ partial English translation).
AU2019243835 Office Action dated Feb. 22, 2024.
CN201980035906.8 Decision of Rejection dated Feb. 4, 2024 (w/ English translation).
JP2021-502711 Office Action dated Nov. 2, 2023 (w/ English translation).
JP2021-502711 Office Action dated Mar. 14, 2023 (w/ English translation).
Ge et al. High-Throughput Density Measurement Using Magnetic Levitation. J. Am. Chem. Soc. 140, 7510-7518 (Jun. 11, 2018).
SG11202009547S Written Opinion dated Jun. 19, 2023.
EP19777208.0 Extended European Search Report dated Nov. 26, 2021.
CN201980035906.8 Office Action and Search Report dated Jul. 20, 2022 (w/ English translation).
SG11202009547S Search Report and Written Opinion dated Sep. 29, 2021.
SG11202009547S Office Action dated Mar. 20, 2024.
Esmaeili et al. Hybrid Magnetic-DNA Directed Immobilisation Approach for Efficient Protein Capture and Detection on Microfluidic Platforms. Scientific Reports 7:194 (Mar. 15, 2017). 11 pages.
PCT/US2019/024138 International Search Report and Written Opinion dated Jul. 19, 2019.
Wilbanks et al. Exploiting magnetic asymmetry to concentrate diamagnetic particles in ferrofluid microflows. Journal of Applied Physics 115, 044907 (2014). Published online Jan. 27, 2014. 7 pages.
JP2021-502711 Office Action dated Jul. 23, 2024 (English translation).
JP2023-149214 Office Action dated Aug. 14, 2024 (English translation).
EP19777208.0 Examination Report dated Jun. 20, 2025.
JP2023-149214 Office Action dated May 19, 2025 (English Translation).

\* cited by examiner

Prior Art

FIG. 3A
Prior art
FIG. 3B
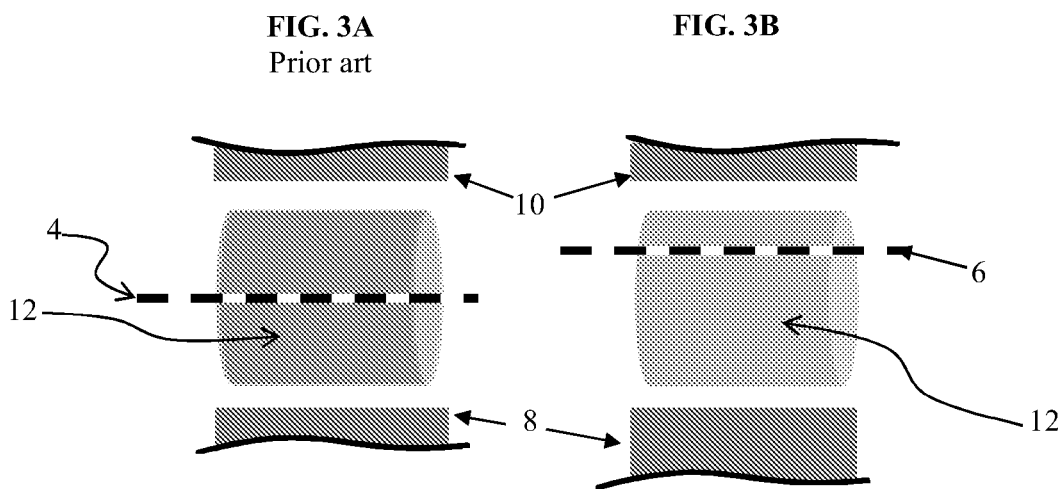
FIG. 4A
FIG. 4B
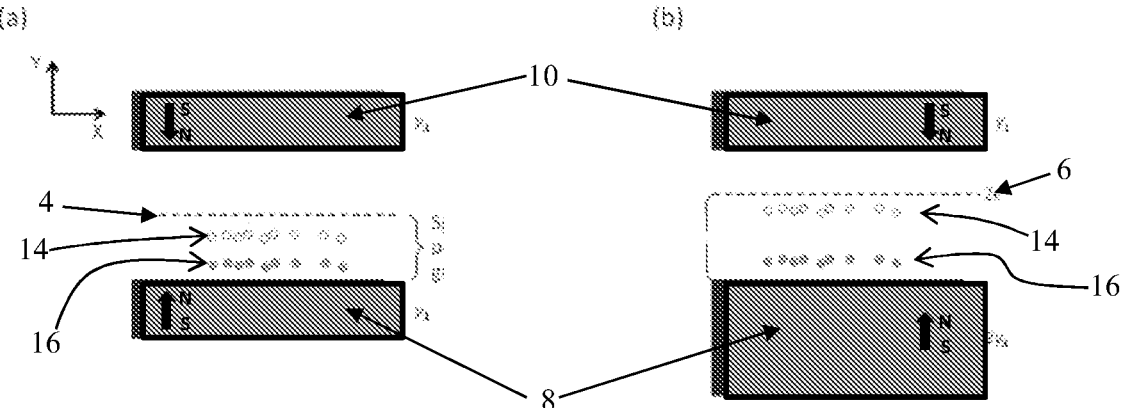

FIG. 7                                     FIG. 8
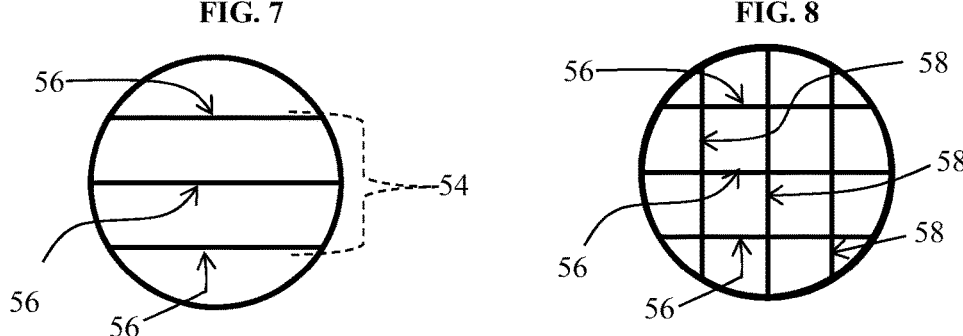
FIG. 9
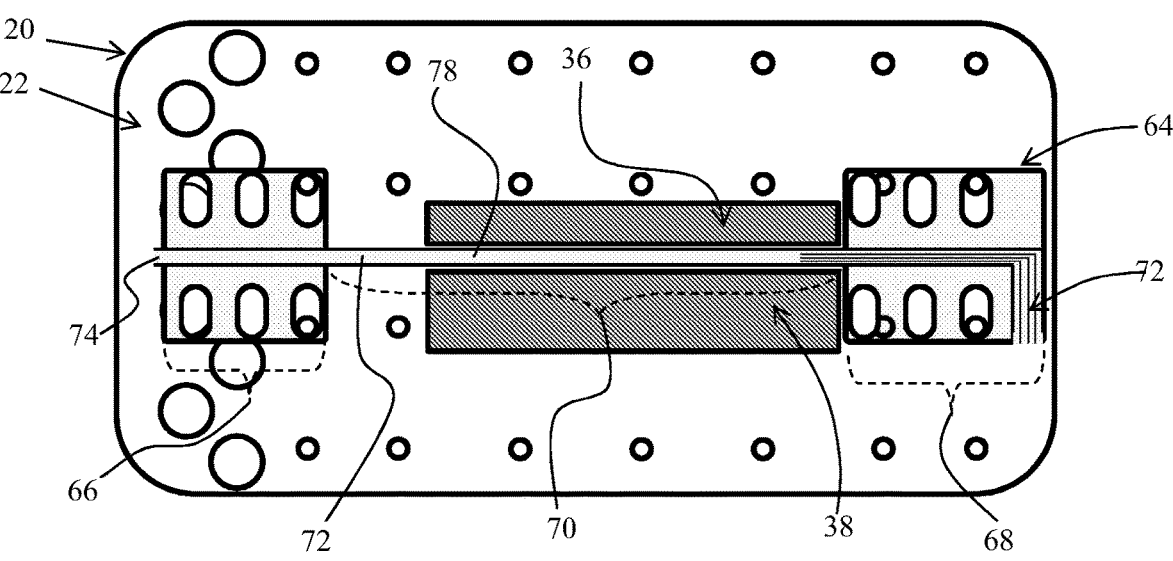

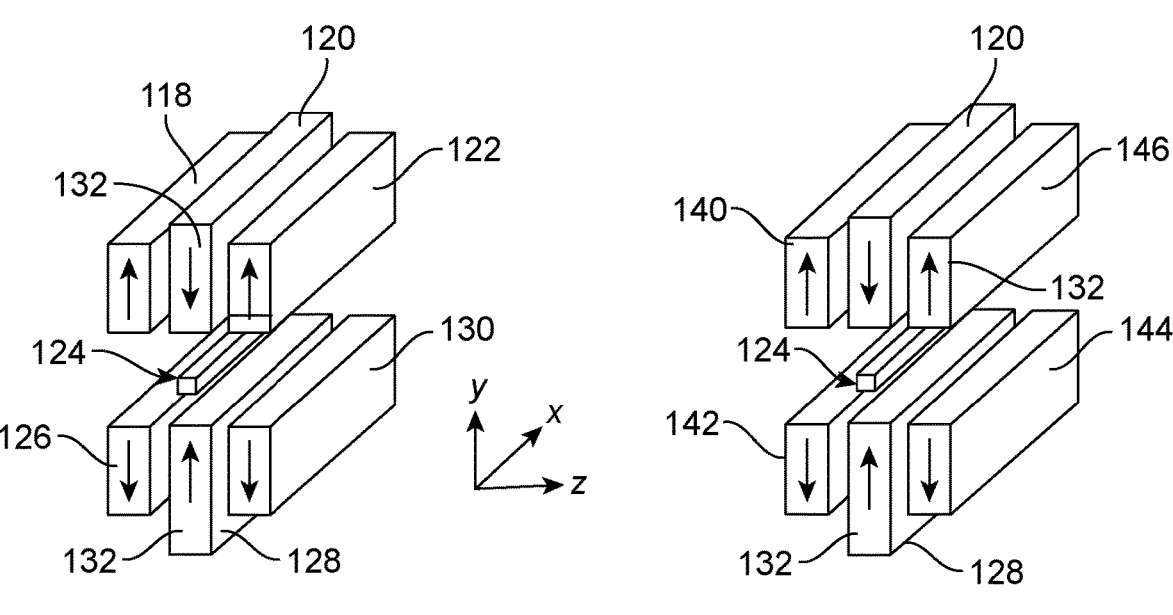
FIG. 17A                    FIG. 17B
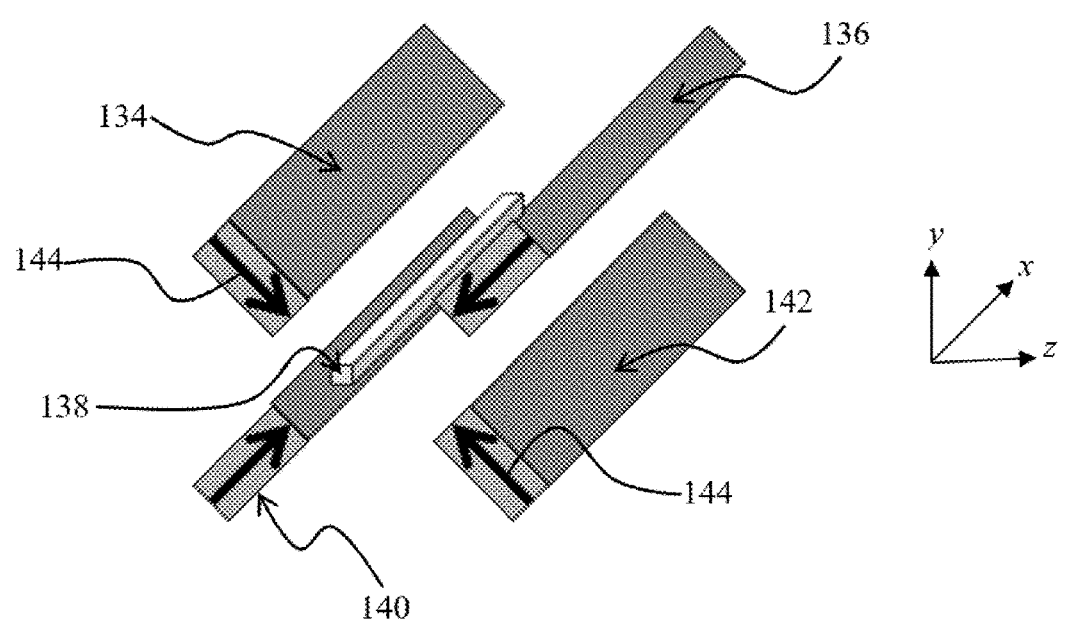
FIG. 18

MAGNETIC PARTICLE ISOLATION DEVICE AND METHODS OF USE

CROSS-REFERENCE

This application is a continuation of International Application No. PCT/US2019/024138, filed Mar. 26, 2019, which claims the benefit of U.S. Provisional Application No. 62/648,300, filed Mar. 26, 2018, and U.S. Provisional Application No. 62/728,684, filed Sep. 7, 2018, each of which is herein incorporated by reference in its entirety.

TECHNICAL FIELD OF THE INVENTION

The present invention relates generally to the magnetic levitation of particles, such as cells or biomolecules, in order to isolate such particles within a medium.

BACKGROUND OF THE INVENTION

Isolation of particles contained within a medium is an important step in many chemical and biological processes. In some processes there may be a need to simply isolate a particle to facilitate the use or manipulation of the particle, whereas in other processes there may be a need to separate the particle from other particles that are also present in the medium. Devices can rely on the magnetic properties of the particles and their surrounding medium in order to separate out particles of interest from heterogenous populations of particles.

For example, a levitation system can have a microcapillary channel that is positioned between a set of two magnets. A heterogeneous population of cells in a magnetically-responsive medium can be sent through the microcapillary channel and can be exposed to a magnetic field created by the two adjacent magnets. Upon exposure to the magnetic field cells of the same type within the heterogeneous population of cells can levitate to a specific height within the microcapillary channel, thereby separating cells from one another. The levitation height of a given cell can be determined based on the balancing of magnetic force and corrected gravitational force on the individual cells.

The two magnets can be positioned symmetrically relative to the capillary channel so that the magnetic field strength distribution is symmetric with respect to each axis of the capillary channel. In some cases, a symmetrical configuration of magnets can limit the capabilities of a device to separate particles. In some cases, with a vertically symmetric configuration of magnets, all of the particles in the magnetically-responsive medium which are denser than the medium itself can levitate to positions below the symmetry axis (i.e., the vertical midpoint between the two magnets). This can have two consequences: (1) the spread of levitation heights can be constrained to half of the available space between the magnets; and (2) fluidic paths can be captured within a smaller space (i.e., the lower half of the channel), which can pose difficulties in fabrication and can increase flow resistance. Moving the magnets further apart and using a larger capillary, all other factors being consistent, can result in shallower field gradients, which can result in weaker separating forces on the particles.

Accordingly, there is a need for a cell isolation device that improves selectivity by increasing the spread of levitation positions for a given surface strength of magnet and improves the manufacturability and operability of fluidic devices coupled to the levitation region.

SUMMARY OF THE INVENTION

The inventive embodiments provided in this Summary of the Invention are meant to be illustrative only and to provide an overview of selected embodiments disclosed herein. The Summary of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

Provided herein is a particle isolation device that includes a fluidic channel and two magnetic components that are positioned on opposite sides of the fluidic channel along a substantially vertical axis, wherein the two magnetic components are configured to create an asymmetric magnetic field within the fluidic channel.

Also provided herein is a particle isolation device having a fluidic channel structure, at least two magnetic components, and one or more pumps configured to drive fluid from an input port through the fluidic channel structure, and out an output port. In accordance with this embodiment the fluidic channel structure includes at least one input port and at least one output port interconnected by a fluidic channel, wherein the fluidic channel includes a substantially linear portion that includes a leading end that is in fluidic communication with the input port and a terminal end that is in fluidic communication with the output port. This embodiment further includes two magnetic components that are substantially vertically positioned on opposite sides of the substantially linear portion of the fluidic channel, wherein the two magnetic components are configured to create an asymmetric magnetic field within the substantially linear portion of the fluidic channel.

Further provided herein is a particle isolation device comprising a fluidic channel structure having at least one input port and at least two output ports interconnected by a series of fluidic channels, wherein the series of fluidic channels include a first, a second, and a third substantially linear portion. In accordance with this embodiment the fluidic channel structure includes a first processing pathway and a second processing pathway. The first processing pathway extends from an inlet port to a first substantially linear portion and from the first substantially linear portion to the second substantially linear portion and from the second substantially linear portion to an outlet port. The second processing pathway extends from an inlet port to a first substantially linear portion and from the first substantially linear portion to a third substantially linear portion and from the third substantially linear portion to an outlet port. The device further includes a first, a second, and a third pair of magnetic components that are substantially vertically positioned on opposite sides of the first, the second, and third substantially linear portion of the fluidic channel, respectively, wherein at least one of the pair of magnetic components is configured to create an asymmetric magnetic field within its adjacent substantially linear portion of the fluidic channel. The device further includes one or more pumps configured to drive fluid from at least one input port through the fluidic channel and out at least one output port.

In one aspect, the magnetic components of the particle isolation device create a magnetic field within the fluidic channel that is asymmetric, and preferably asymmetric along a substantially vertical axis.

In another aspect, the particle isolation device comprises two magnetic components that are configured relative to the fluidic channel such that a first magnetic component of the two magnetic components creates a magnetic field within the fluidic channel that is stronger than a magnetic field within the fluidic channel created by a second magnetic component of the two magnetic components.

In another aspect, the particle isolation device includes two magnetic components that are permanent magnets or electromagnets. The magnetic components may comprise a permanent bar magnet comprising neodymium-iron, samarium-cobalt, aluminum-iron-cobalt alloys, or ferrite.

In another aspect, the particle isolation device includes two magnetic components, including an upper magnet and a lower magnet, where the upper magnet is larger than the lower magnet or the lower magnet is larger than the upper magnet.

In another aspect, the particle isolation device includes a splitter that partitions the fluidic channel into at least two channels. In an embodiment, the splitter is positioned within the fluidic channel at the terminal end of the substantially linear portion of the fluidic channel, and divides the fluidic channel into two or more channels. In an embodiment, the splitter is located within the fluidic channel such that the fluidic channel is split at a position that is between the two magnetic components. In an embodiment, the splitter partitions the fluidic channel into a plurality of vertically spaced channels.

In a further aspect, the particle isolation device comprises an integrated fluidic chip or cartridge.

In another aspect, the particle isolation device includes one or more valves to control the flow of fluid within the fluidic channel and/or the flow of fluid into at least one input port or from at least one output port.

In another aspect, the particle isolation device includes a device for visualizing and/or recording images of particles as they pass through the asymmetric magnetic field.

Further provided herein is a particle isolation device comprising one or more processing segments with each processing segment comprising a substantially linear fluidic channel portion flanked by a pair of magnetic components, whereby the processing segments are in fluidic communication with one another in parallel or in series.

In an aspect of the invention, the particle isolation device incudes a fluidic channel structure having multiple substantially linear portions, where a first pair of magnetic components is configured to create a symmetric magnetic field within the fluidic channel of a first substantially linear portion, and a second pair of magnetic components is configured to create an asymmetric magnetic field within the fluidic channel of a second substantially linear portion, and a third pair of magnetic components is configured to create an asymmetric magnetic field within the fluidic channel of the third substantially linear portion. In accordance with an embodiment, the first substantially linear portion is in serial fluidic communication with the second and third substantially linear portions, and the second and third substantially linear portions are configured in parallel and are not in direct fluid communication.

In one aspect, the first pair of magnetic components includes a first upper bar magnet positioned above the first linear portion and a first lower bar magnet positioned below the first substantially linear portion and the first upper magnet and first lower magnet are positioned in a magnetic repelling orientation, and wherein the second pair of magnetic components comprise a second upper bar magnet positioned above the second substantially linear portion and a second lower bar magnet positioned below the second substantially linear portion and the second upper magnet and second lower magnet are positioned in a magnetic repelling orientation, and wherein the third pair of magnetic components comprise a third upper bar magnet positioned above the third substantially linear portion and a third lower bar magnet positioned below the third substantially linear portion and the third upper magnet and third lower magnet are positioned in a magnetic repelling orientation. In a further aspect, the second upper bar magnet emits a stronger magnetic field than the second lower bar magnet, and the third lower bar magnet emits a stronger magnetic field than the third upper bar magnet. In a further aspect, the second upper bar magnet comprises two or more magnets that emit a stronger magnetic field than the second lower bar magnet, and the third lower bar magnet comprises two or more magnets that emit a stronger magnetic field than the third upper bar magnet.

In another aspect, the particle isolation device comprises one or more sets of parallel fluidic channels that share one or more central or interspersed magnets. The magnets are positioned to shape the magnetic field in each separate fluidic channel, and the opposing magnets for each separate fluidic channel are positioned such that identical poles are facing (i.e., S-S or N-N).

In another aspect, the particle isolation device comprises a set of one or more wells for performing static separations in an assay format. Neighboring wells may share one or more magnets, e.g., stacked magnets, to create a magnetic field, e.g., a shaped magnetic field that isolates particles in the medium, e.g., into the center of the medium.

In another aspect, the particle isolation device further comprises a first splitter that begins along a trailing end of the fluidic channel within the first substantially linear portion, a second splitter that begins along a trailing end of the fluidic channel within the second substantially linear portion, and a third splitter that begins along a trailing end of the fluidic channel within the third substantially linear portion. In a further aspect, the first splitter splits the fluidic channel along the first substantially linear portion into at least two fluidic channels, whereby one of said at least two fluidic channels is in fluidic communication with the fluidic channel within the second substantially linear portion and the one of said at least two fluidic channels is in fluidic communication with the fluidic channel within the third substantially linear portion. In another aspect, the second splitter splits the fluidic channel along the second substantially linear portion into at least two fluidic channels, whereby said at least two fluidic channels is in fluidic communication with a corresponding outlet port. In a further aspect, the third splitter splits the fluidic channel along the third substantially linear portion into at least two fluidic channels, whereby said at least two fluidic channels is in fluidic communication with a corresponding outlet port.

In an embodiment of the present invention, there is provided a method of isolating particles. The method comprises the steps of: (a) forming a processing solution comprising particles and a paramagnetic medium, (b) passing the processing solution through a particle isolation device, where the device includes a fluidic channel structure including a fluidic channel, and at least two magnetic components that are positioned on opposite sides of the fluidic channel, and where the two magnetic components create an asymmetric magnetic field within the fluidic channel, thereby isolating the particles as they pass through the asymmetric magnetic field, thereby generating isolated particles, and (c) observing, analyzing, recording, and/or collecting the isolated particles.

In one aspect, the method of the present invention is practiced with the fluidic channel structure including at least one input port and at least one output port interconnected by the fluidic channel, wherein the fluidic channel includes a substantially linear portion having a leading end that is in fluidic communication with the input port and a terminal end that is in fluidic communication with the output port, where the at least two magnetic components that are substantially vertically positioned on opposite sides of the substantially linear portion of the fluidic channel, where the at least two magnetic components are configured to create an asymmetric magnetic field within the substantially linear portion of the fluidic channel, and, optionally, one or more pumps configured to drive fluid from the at least one input port through the fluidic channel and out the at least one output port, and wherein the method further comprises pumping the processing solution through the fluidic channel, and where the observing, analyzing, and/or recording the isolated particles includes observing, analyzing, and/or recording the isolated particles along the substantially linear portion of the fluidic channel, and/or collecting the isolated particles from the at least one output port.

In a further aspect, the paramagnetic medium comprises a paramagnetic material and a solvent. In another aspect, the paramagnetic medium comprises a paramagnetic material, salts, and other additives that function to maintain cellular integrity. In another aspect, the paramagnetic medium is biocompatible.

In a further aspect, the paramagnetic material may include gadolinium, titanium, vanadium, chromium, manganese, iron, nickel, gallium, dysprosium, ions thereof, or combinations thereof. In a further aspect, the paramagnetic material includes titanium (III) ion, gadolinium (III) ion, vanadium (I) ion, nickel (II) ion, chromium (III) ion, dysprosium (III) ion, vanadium (III) ion, cobalt (II) ion, or gallium (III) ion. In a further aspect, paramagnetic material comprises a chelated compound. In a further aspect, the paramagnetic material comprises a gadolinium chelate, a dysprosium chelate, or a manganese chelate.

In another aspect, the paramagnetic material is present in the paramagnetic medium at a concentration of at least 10 mM, 20 mM, 30 mM, 40 mM, 50 mM, 60 mM, 70 mM, 80 mM, 90 mM, 100 mM, 120 mM, 150 mM, 200 mM, 250 mM, 300 mM, 500 mM, or 1 M. In a further aspect, the paramagnetic material is present in the paramagnetic medium at a concentration of about 10 mM to about 50 mM, about 25 mM to about 75 mM, about 50 mM to about 100 mM, about 100 mM to about 150 mM, about 150 mM to about 200 mM, about 200 mM to about 250 mM, about 250 mM to about 300 mM, about 300 mM to about 500 mM, or about 500 mM to about 1 M.

In another aspect, the paramagnetic material comprises gadolinium and is present in the paramagnetic medium at a concentration of at least about 10 mM, 20 mM, 30 mM, 40 mM, 50 mM, 60 mM, 70 mM, 80 mM, 90 mM, or 100 mM. In a further aspect the paramagnetic material comprises gadolinium and is present in the paramagnetic medium at a concentration of about 10 mM to about 50 mM, about 25 mM to about 75 mM, or about 50 mM to about 100 mM.

In another aspect, the at least two magnetic components comprise an upper magnet and a lower magnet, and where a density of the particles is greater than a density of the paramagnetic material, and a magnetic field created by the lower magnet is greater than the magnetic field created by the upper magnet. In another aspect, the density of the particles is less than the density of the paramagnetic material, and the magnetic field created by the lower magnet is less than a magnetic field created by the upper magnet.

In another aspect, as the processing fluid passes through the asymmetric magnetic field, the particles of interest will reach a substantially similar equilibrium height. In a further aspect, the at least two magnetic components comprise an upper magnet and a lower magnet, and wherein substantially all of the particles contained within the processing solution reach an equilibrium height where a difference between the highest equilibrium height of the particles and a lowest equilibrium height of the particles (i.e., the equilibrium height distribution) is equal to less than 35% of a vertical gap between the upper magnet and lower magnet, or less than 30% of the vertical gap between the upper magnet and lower magnet, or less than 25% of a vertical gap between the upper magnet and lower magnet, or less than 20% of a vertical gap between the upper magnet and lower magnet, or less than 15% of a vertical gap between the upper magnet and lower magnet, or less than 10% of a vertical gap between the upper magnet and lower magnet, or less than 8% of a vertical gap between the upper magnet and lower magnet, or less than 6% of a vertical gap between the upper magnet and lower magnet, or less than 5% of a vertical gap between the upper magnet and lower magnet. In an aspect, an equilibrium height distribution of substantially all the particles of interest is less than about 5000 microns, 4000 microns, 3000 microns, 2000 microns, 1000 microns, 500 microns, 300 microns, or 200 microns, or the equilibrium height distribution of substantially all of the particles of interests is about 1 micron to about 5000 microns, or about 1 micron to about 3000 microns, or about 1 micron to about 1000 microns, or about 1 micron to about 500 microns, or about 1 micron to about 200 microns.

In accordance with a method of the present invention, once substantially all the particles reach an equilibrium height, the particles pass through a splitter that geometrically divides the processing solution into multiple effluent fractions, and the effluent fraction or fractions containing substantially all the particles are collected, thereby isolating the particles. In an aspect of the invention, the substantially all the particles includes at least approximately 70%, 75%, 80%, 85%, 90%, or 95% of the particles.

In another aspect, the method of the invention further comprises a step of separating the isolated particles from the paramagnetic medium. In another aspect, the particles comprise a biomolecule, cell, cluster of cells, protein, lipid, carbohydrate, microorganism, or bacteria.

In accordance with an embodiment, a method of isolating particles is provided comprising: (a) forming a processing solution comprising the particles and a paramagnetic medium, (b) passing the processing solution through a particle isolation device, where the device comprises a fluidic channel structure including a series of fluidic channels and at least two processing segments, where each processing segment of the at least two processing segments includes at least two magnetic components that are positioned on opposite sides of a portion of the fluidic channel, and where the two magnetic components create an asymmetric magnetic field within their corresponding portion of the fluidic channel, whereby a portion of the processing solution passes through the at least two processing segments in parallel, and/or a portion of the processing solution or all of the processing solution passes through at least two processing segments in series, thereby isolating the particles as they pass through the asymmetric magnetic fields of the processing segments, and (c) observing, analyzing, recording, and/or collecting the isolated particles.

In an aspect, the method of the present invention includes a fluidic channel structure includes at least one input port and at least two output ports interconnected by the series of fluidic channels, wherein the series of fluidic channels includes a first substantially linear portion, a second substantially linear portion, and a third substantially linear portion, where the fluidic channel structure includes: (i) a first processing pathway extending from the at least one inlet port to the first substantially linear portion and from the first substantially linear portion to the second substantially linear portion and from the second substantially linear portion to an output port of the at least two output ports, and (ii) a second processing pathway extending from the at least one inlet port to the first substantially linear portion and from the first substantially linear portion to the third substantially linear portion and from the third substantially linear portion to an output port of the at least two output ports, a first pair of magnetic components, a second pair of magnetic components, and a third pair of magnetic components that are substantially vertically positioned on opposite sides of the first substantially linear portion, the second substantially linear portion, and third substantially linear portion, respectively, where at least one of the first pair of magnetic components, second pair of magnetic components, and third pair of magnetic components is configured to create an asymmetric magnetic field within its adjacent substantially linear portion, and one or more pumps configured to drive fluid from the at least one input port through the series of fluidic channels and out the at least two output ports; and the method comprises passing a portion of the processing solution through the first processing pathway, and a portion of the processing solution through the second processing pathway, whereby there is a first isolation of particles as the particles pass through the asymmetric magnetic field in the first substantially linear portion, and there is a second isolation of particles as they pass through the asymmetric magnetic fields of either the second substantially linear portion or the third substantially linear portion.

BRIEF DESCRIPTION OF THE DRAWINGS

FIGS. 3A and 3B are an illustration of the shifting neutral line resulting from the asymmetric magnetic field in accordance with the present invention.

FIGS. 4A and 4B are an illustration of the impact of the shifting neutral line on the isolation of particles in accordance with the present invention.

FIG. 7 is a cross-sectional view of capillary 32 of the trailing end 60 of processing segment 50 taken along line 7-7 in FIG. 5.

FIG. 8 is an alternative embodiment of a cross-sectional view of capillary 32 of the trailing end 60 of processing segment 50 taken along line 7-7 in FIG. 5.

FIG. 9 is a plane view of an alternative embodiment of a particle isolation device in accordance with the present invention.

FIGS. 17A and 17B are perspective views of alternative magnet configurations of a particle isolation device in accordance with the present invention.

FIG. 18 is a perspective view of an alternative magnet configuration of a particle isolation device in accordance with the present invention.

DETAILED DESCRIPTION OF THE INVENTION

I. Definitions/Nomenclature

Figure 1:
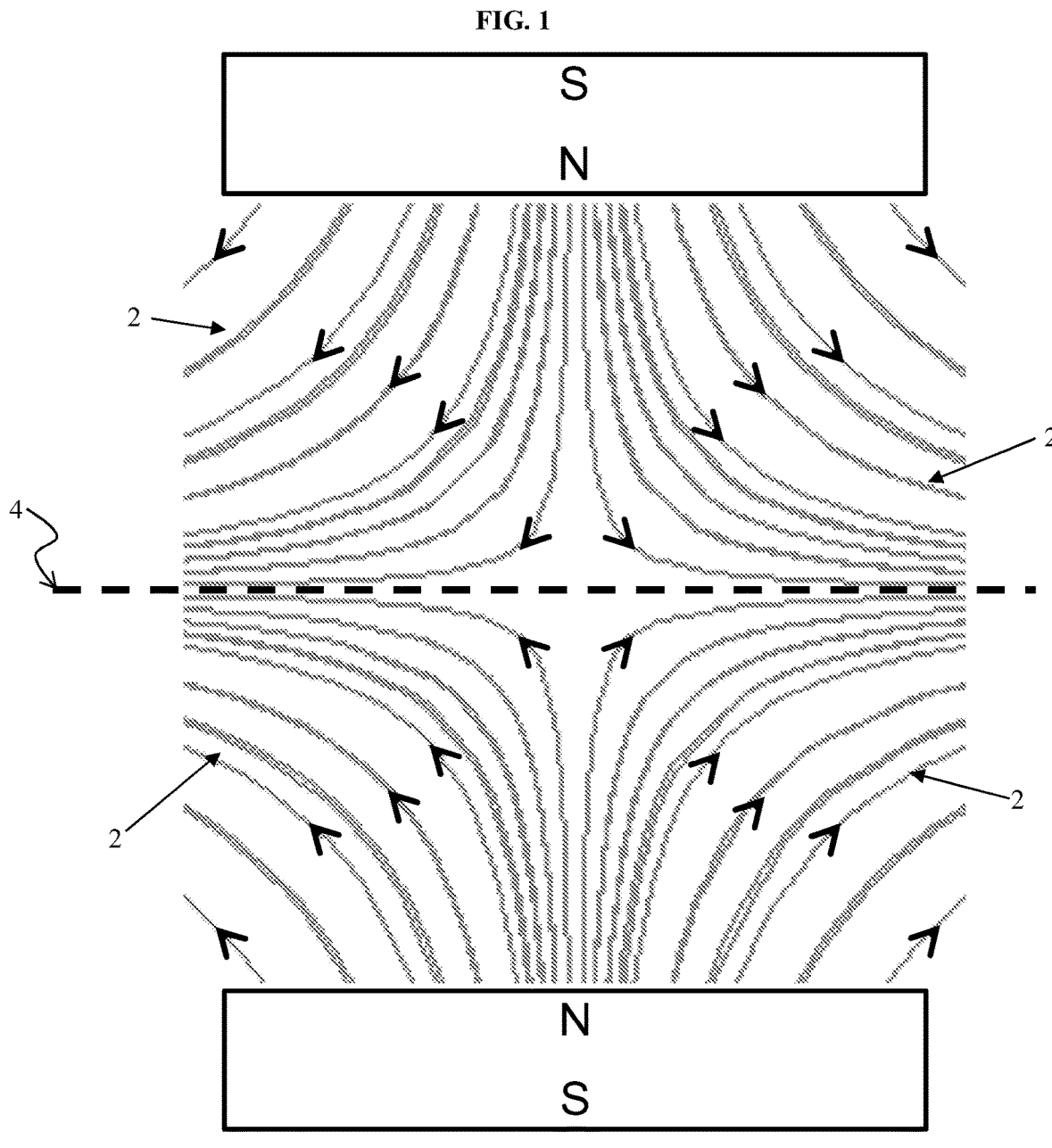
FIG. 1 is an illustration of the magnetic fields in present in prior art devices.

The following definitions are provided to aid in understanding the invention. Unless otherwise defined, all terms of art, notations and other scientific or engineering terms or terminology used herein are intended to have the meanings commonly understood by those of skill. In some cases, terms with commonly understood meanings are defined herein for clarity and/or for ready reference, and the inclusion of such definitions herein should not be assumed to represent a substantial difference over what is generally understood in the art but is intended to compliment such general understandings. To the extent a definition herein is inconsistent with what is generally understood in the art, unless expressly stated otherwise, both the definition provided herein and what is generally understood in the art shall be deemed to be within the scope of the present invention as alternative embodiments.

As used herein unless otherwise indicated, open terms such as "contain," "containing," "include," "including," and the like mean comprising.

Some embodiments herein contemplate numerical ranges. When a numerical range is provided, the range includes the range endpoints unless otherwise indicated. Unless otherwise indicated, numerical ranges include all values and subranges therein as if explicitly written out.

As used herein, the article "a" means one or more unless explicitly stated otherwise.

Some values herein are modified by the term "about." In some instances, the term "about" in relation to a reference numerical value can include a range of values plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value. Where a series of values is prefaced with the term "about," the term is intended to modify each value included in the series.

As used herein, the term "asymmetric" about a magnetic field means that the magnetic field in the region of an associated fluidic channel is not symmetric about one or more planes passing through the center of the fluidic channel, and in accordance with a preferred embodiment it is not symmetric about the horizontal plane.

As used herein, the terms "capillary," "microcapillary," or "capillary tube" refer to a tube having a channel as defined herein below.

As used herein, the terms "channel", "flow channel," "fluid channel" and "fluidic channel" are used interchangeably and refer to a pathway on a fluidic device in which a fluid can flow. Channel includes pathways with a maximum internal dimension (e.g. height or thickness) of about 30 mm, about 25 mm, about 20 mm, about 15 mm, about 10 mm, about 5 mm, about 5 mm, about 3 mm, about 2 mm, about 1 mm, or about 0.5 mm. The internal height of the channel may not be uniform across its cross section, and geometrically the cross section may be any shape, including round, square, oval, rectangular, or hexagonal. The term "channel" includes, but is not limited to, microchannels and nanochannels, and with respect to any reference to a channel herein, such channel may comprise a microchannel or a nanochannel.

As used herein, the term "concentration" means the amount of a first component contained within a second component, and may be based on the number of particles per unit volume, a molar amount per unit volume, weight per unit volume, or based on the volume of the first component per volume of the combined components.

As used herein, the term "fluidically coupled" or "fluidic communication" means that a fluid can flow between two components that are so coupled or in communication.

As used herein, the terms "isolate" or "isolating" in reference to a component means separating such component from other components, and includes increasing the concentration of a component within a solution, or separating a component from other components in a solution, or a combination of both increasing the concentration of a component within a solution while separating such component from other components in the solution. A particle within a solution is deemed "isolated" if it is segregated from other particles within the solution and/or positioned within a defined portion of the solution. A particle or component within a solution is also deemed "isolated" if after processing the solution the concentration of such particle or component is increased by a ratio of at least about 100:1, 90:1, 80:1, 70:1, 60:1, 50:1, 40:1, 30:1, 20:1, 10:1, 5:1, or 2:1. Particles of interest within a solution containing other particles are deemed "isolated" if after processing such solution the ratio of the concentration of such particles of interest to the concentration of such other particles is increased, or if the ratio of the concentration of such particles of interest to the concentration of such other particles is increased by at least about 50%, 100%, 200%, 300%, 400%, 500%, 600%, 700%, 800%, 900%, or 1000%, or if the concentration of such other components is decreased to less than about 50%, 20%, 15%, 10%, 8%, 6%, 5%, 4%, 3%, 2%, 1%, or 0.5%, with respect to their initial concentration or as a proportion of particles of a similar size that remain present.

As used herein, the term "fluidic" refers to a system, device or element for handling, processing, ejecting and/or analyzing a fluid sample including at least one "channel" as defined hereinabove. The term "fluidic" includes, but is not limited to, microfluidic and nanofluidic.

As used herein, the term "fluidic function" refers to any operation, function or process performed or expressed on a fluid or sample in a fluidic system, including, but not limited to filtration, pumping, fluid flow regulation, controlling fluid flow and the like.

As used herein, the term "particle" refers to any matter, including, but not limited to atoms, chemical elements, molecules, compounds, biomolecules, cells, proteins, lipids, carbohydrates, microorganisms, bacteria, or any physical substance with its largest dimension in any direction being less than about 3 mm, 2 mm, 1 mm, 0.5 mm, 0.25 mm, 100 microns, 75 microns, 50 microns, 40 microns, 30 microns, 20 microns, or 10 microns.

As used herein, the term "port" refers to a structure for providing fluid communication between two elements using, for example, a fluidic channel.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

II. Asymmetric Magnetic Field

The present disclosure provides a device for isolating particles by using magnetic levitation. Magnetic levitation refers to the use of a magnetic field to counter the force of gravity on particles, thereby causing like particles to ascend or descend to an equilibrium height within a medium. The equilibrium height for any given particle can be determined by numerous factors including the relative magnetic susceptibility of the particles and the medium, the relative densities of the particles and the medium, the size of the particles and the strength of the magnetic field. Once like particles reach their equilibrium height various fractions can then be collected to isolate the like particles, or alternatively various treatments can then be targeted to one or more fractions thereby isolating such treatments to the like particles within such fraction(s). In accordance with a preferred embodiment, such fractions comprise substantially vertical fractions along the height of a fluidic channel containing the particles and the medium.

In an embodiment, the device includes a fluidic channel and a magnetic field source that is configured to exert an asymmetric magnetic force along at least a portion of the fluidic channel. The asymmetry of the magnetic force exists at least along one axis of the fluidic channel. Preferably, the magnetic force is asymmetric at least along the vertical axis of the fluidic channel. Alternatively, the magnetic force is asymmetric only along the vertical axis of the fluidic channel. In other embodiments of the present invention, the magnetic force is asymmetric along the vertical axis of the fluidic channel and at least one additional axis of the fluidic channel, or the magnetic force is asymmetric along all three axes of the fluidic channel.

In accordance with prior art devices, identical magnets are symmetrically placed above and below a fluidic channel in a repelling orientation relative their magnetic poles, thereby resulting in a symmetric magnetic force along the vertical axis of the fluidic channel. The magnetic field lines 2 of two opposing identical magnets in accordance with such prior art devices are illustrated in FIG. 1. As shown in FIG. 1, when identical magnets are utilized, the neutral line 4 (or zero field plane) wherein the forces exerted by the two opposing magnets cancel each other out will occur at a vertical position that is half way between the two magnets.

Figure 2:
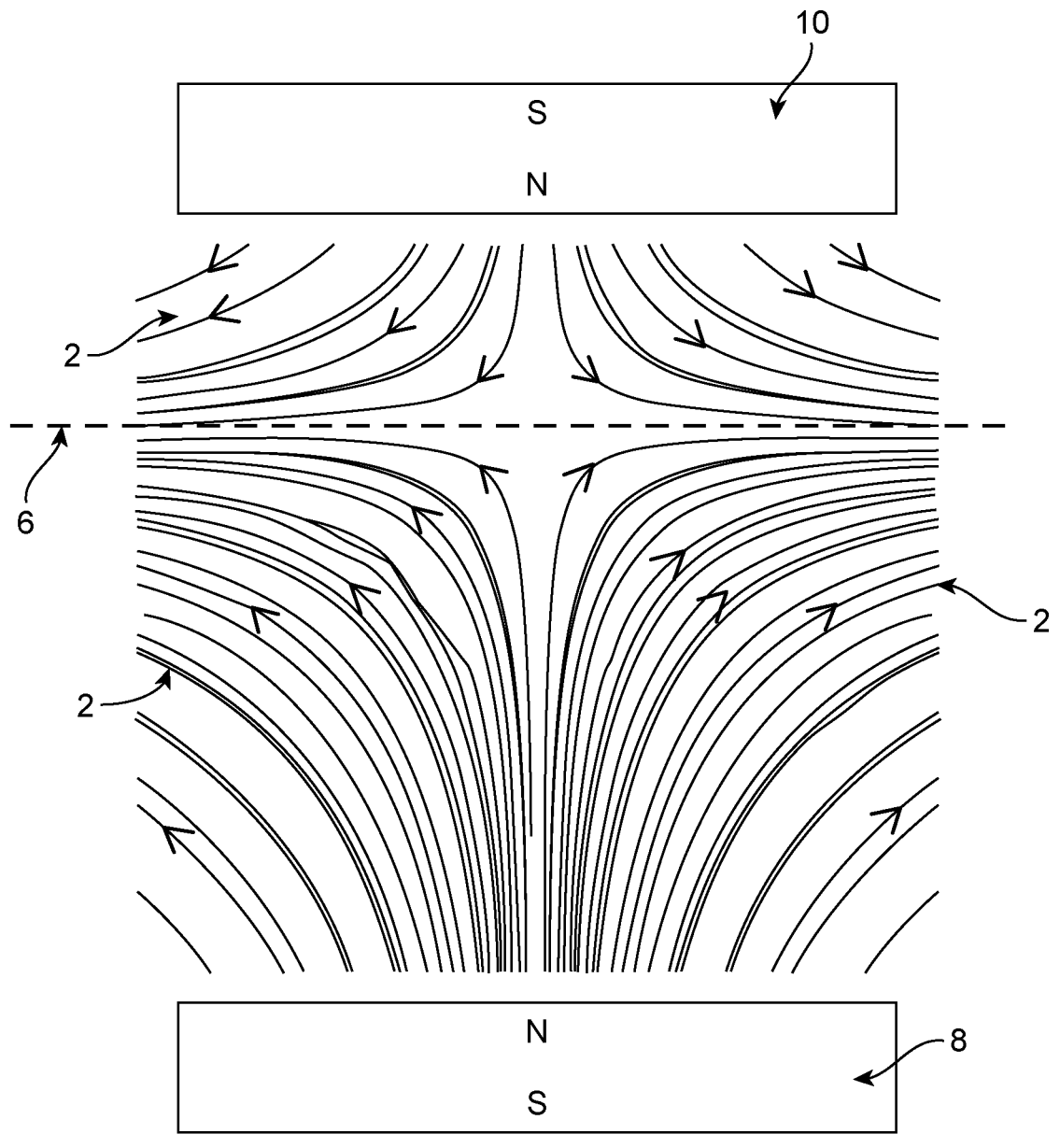
FIG. 2 is an illustration of the magnetic fields present in the device in accordance with the present invention.

In accordance with an embodiment of the present invention, a magnet configuration is used wherein the force exerted on a particle on one side of the fluidic channel is greater than the force exerted on an identical particle on the other side of the fluidic channel, thereby resulting in an asymmetric magnetic force perpendicular to the fluidic channel. This force imbalance may be achieved by using one stronger magnet or using a plurality of magnets on one side of the fluidic channel. A stronger magnet may be achieved by using a single magnet with similar geometry but stronger internal magnetization, or a magnet with a greater axial dimension and the same magnetization. FIG. 2 illustrates the magnetic field lines 2 of two opposing magnets, wherein the lower magnet 8 is stronger than the upper magnet 10 in accordance with the present invention. As illustrated in FIG. 2, neutral line 6 vertically shifts or is biased towards the weaker magnet. FIGS. 3A and 3B illustrate how this neutral line shift would impact the magnetic field lines 2 that occur in a fluidic channel 12 interposed between an upper magnet 10 and a lower magnet 8. FIG. 3A illustrates the prior art configuration, and FIG. 3B illustrates the configuration in accordance with the present invention. As illustrated in FIG. 3B the use of a larger magnet under the fluidic channel causes the neutral line 6 to shift or be biased upward toward the weaker upper magnet 10 as compared to the configuration show in FIG. 3A wherein the magnets have the same magnetic strength and impose a symmetric magnetic field resulting in symmetric neutral line 4 that occurs at the vertical midpoint between the two magnets.

For a given grade of magnet, magnetized fully during manufacture, the surface field strength at a pole surface increases with the magnet's dimension in the direction parallel with magnetization. Therefore, by keeping two of the magnet dimensions fixed but increasing the length in the separation or field axis (i.e., vertical axis), the strength of the magnet can be increased. In a symmetric configuration, this can simply increase the field or gradient at any point. In an asymmetric configuration where only the bottom magnet, for example, is increased, the zero field plane or neutral line between the opposing magnets can be pushed towards the weaker magnet (upwards).

FIGS. 4A and 4B illustrate an example of how the vertical shift in the neutral line 4, 6 impacts the operation of the levitation device in accordance with the present invention in order to isolate a first particle 14 and a second particle 16. In particular, in accordance with the present invention, particles of interest are combined with a magnetically-responsive medium and passed through the fluidic channel flanked with magnets located above and below the fluidic channel. All the particles in the magnetically-responsive medium which are denser than the medium itself will levitate at positions below the neutral line. As illustrated in FIG. 4B, use of an asymmetric magnetic field in accordance with the present invention, and the resulting shift of the neutral line 6 upward, avoids constraining the spread of levitation heights to just half of the available vertical space between the magnets (as with prior art devices shown in FIG. 4A), and permits a broader field for particle separation and a broader field for optic visualization of the separation. Furthermore, the present invention allows for larger fluid flows since a greater volume of the fluidic channel can be utilized.

Conversely, if the primary particles of interest are less dense than the magnetically responsive medium, a symmetric magnetic field can limit particle isolation to the top half of the fluidic channel. Thus, in such an application a magnetic configuration can be used that imposes a larger magnet field on upper side of the fluidic channel, thereby shifting the neutral line downward.

III. Levitation Device

The levitation device in accordance with the present invention can comprise an input portion, a processing portion, and an output portion. The levitation device may comprise a component configuration wherein each of the input, processing, and output portions comprise interconnected individual components. Alternatively, the levitation device may comprise an integral configuration, where parts of the input, processing, and output portions are integrated into a single component such as, for example, a fluidic chip. Component configurations of a levitation device in accordance with the present invention are illustrated in FIG. 5 to FIG. 6, and integral configurations are illustrated in FIG. 9 to FIG. 16.

A. Component Configuration

Figure 5:
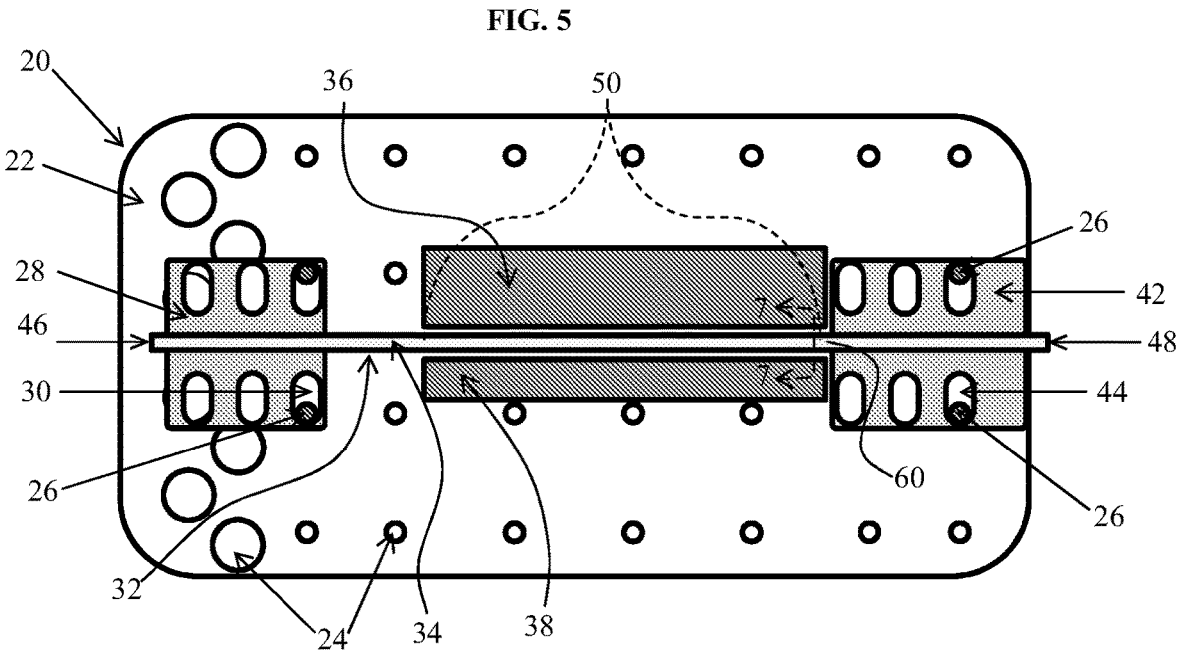
FIG. 5 is a plane view of an alternative embodiment of a particle isolation device in accordance with the present invention.
Figure 6:
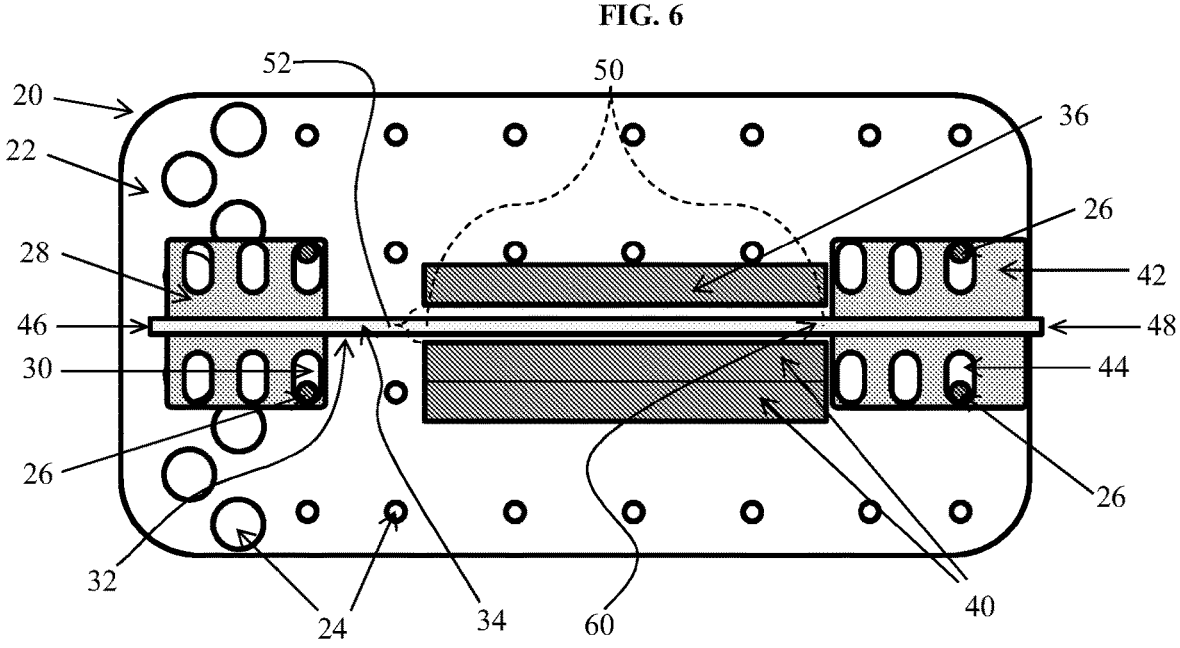
FIG. 6 is a plane view of an alternative embodiment of a particle isolation device in accordance with the present invention.

Referring to FIG. 5, and FIG. 6, various embodiments of a levitation device 20 of the present invention are shown wherein the device's input portion, processing portion, and output portion comprise separate individual components that are interconnected. FIG. 5 illustrates an embodiment wherein an asymmetric magnetic field is achieved by including one larger magnet 36 on one side of a fluidic channel 34. FIG. 6 illustrates an embodiment wherein an asymmetric magnetic field is achieved by including two magnets 40 on one side of a fluidic channel 34, wherein the two magnets 40 are positioned in in an attractive, rather than repelling arrangement. Combining two magnets in the fashion shown in FIG. 6 gives a slightly lower field strength than a monolithic single part 38 as shown in FIG. 5, but still results in an effective asymmetric magnetic field.

Referring to FIG. 5, levitation device 20 includes a support structure and support structure mounting means. In accordance with the illustrated embodiment, the support structure comprises a support structure 22 and the support structure mounting means comprises a plurality of mounting holes 24 and mounting posts 26. The input portion of the device comprises an input manifold 28. The output portion of the device comprises output manifold 42. The input manifold 28 and output manifold 42 are mounted to the support structure 22 using input manifold mounting means 30 and output manifold mounting means 44, respectively, which in accordance with the illustrated embodiment comprise mounting holes and screws. Capillary 32 is mounted on the input and output manifolds via retaining slots contained therein.

The processing portion of the device comprises capillary 32, upper magnet 36 and lower magnet 38. Capillary 32 includes a fluidic channel 34 that extends therethrough along the length of capillary 32. Upper magnet 36 and lower magnet 38 are mounted on support structure 22 so that they are positioned adjacent to fluidic channel 34 with upper magnet 36 positioned above capillary 32 and lower magnet 38 positioned below capillary 32. Upper magnet 36, lower magnet 38, and capillary 32 are substantially horizontally parallel and are aligned along a substantially vertical axis. In accordance with an embodiment, capillary 32 may be vertically centered between upper magnet 36 and lower magnet 38 as illustrated in FIG. 5. Alternatively, capillary 32 may be vertically offset between upper magnet 36 and lower magnet 38 such that it is vertically closer to one of the two magnets as illustrated in FIG. 6.

Upper magnet 36 and lower magnet 38 are configured to create an asymmetric magnetic field within fluidic channel 34. The asymmetric magnetic field is achieved by selecting a magnet configuration wherein the magnetic field created within the fluidic channel from one of the magnets is greater than the magnetic field created by the other magnet. As described in greater detail herein below, this may be achieved by using various different magnetic configurations based on the size of the magnets, the number of magnets, the type of magnets (e.g., magnetic material) or the spacing of the magnets relative to the fluidic channel. As shown in FIG. 5, the upper magnet 36 is larger than the lower magnet 38, and therefore creates a greater magnetic field within fluidic channel 34. As shown in FIG. 6, the lower magnet 38 comprises two smaller magnets which are the same size as the upper magnet 36, and therefore, the combined two lower magnets create a greater magnetic field within fluidic channel 34. In addition, the strength of the magnetic field created within fluidic channel 34 by the lower magnet 38 in FIG. 6 is enhanced by vertically positioning lower magnet 38 closer to fluidic channel 34 than upper magnet 36.

In accordance with an embodiment, capillary 32 comprises an input opening 46 and an output opening 48, and a fluidic channel processing segment 50. The processing segment 50 comprises a substantially linear fluidic channel that is in fluidic communication with input opening 46 and an output opening 48. In some cases, the processing segment 50 is further defined as that portion of the fluidic channel that aligns between upper magnet 36 and lower magnet 38 or 40. Capillary 32 may include a splitter that splits the fluidic channel into a plurality of channels. The splitter is preferably positioned within the processing segment 50, but near the trailing end 60 of the processing segment, so that any particle isolation achieved by passing the fluid between the magnets is maintained as the fluid exits the device. The splitter may comprise one or more substantially horizontal partitions that extend from the trailing end 60 of processing segment 50 to output opening 48. Horizontal partitions 56 of splitter 54 are illustrated in FIG. 7, which is a cross-sectional view of capillary 32 of the trailing end 60 of processing segment 50 taken along line 7-7 in FIG. 5. In accordance with an embodiment incorporating the splitter shown in FIG. 7, four vertical fractions would be collected at output opening 48. In addition, the splitter may include one or more vertical partitions, thereby creating a horizontal and vertical grid (see FIG. 8) of effluent fluidic channels leading to output opening 48.

B. Integral Configuration

Figure 10:
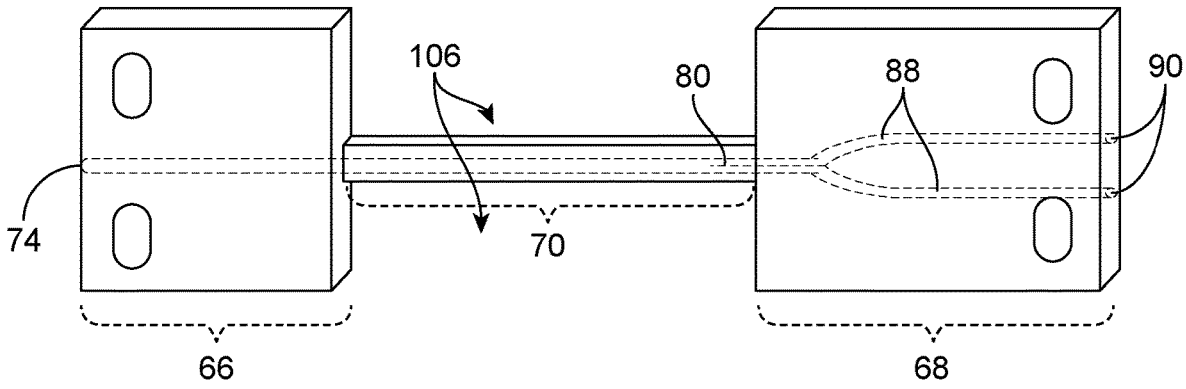
FIG. 10 is a perspective view of an alternative embodiment of a particle isolation device in accordance with the present invention.
Figure 11:
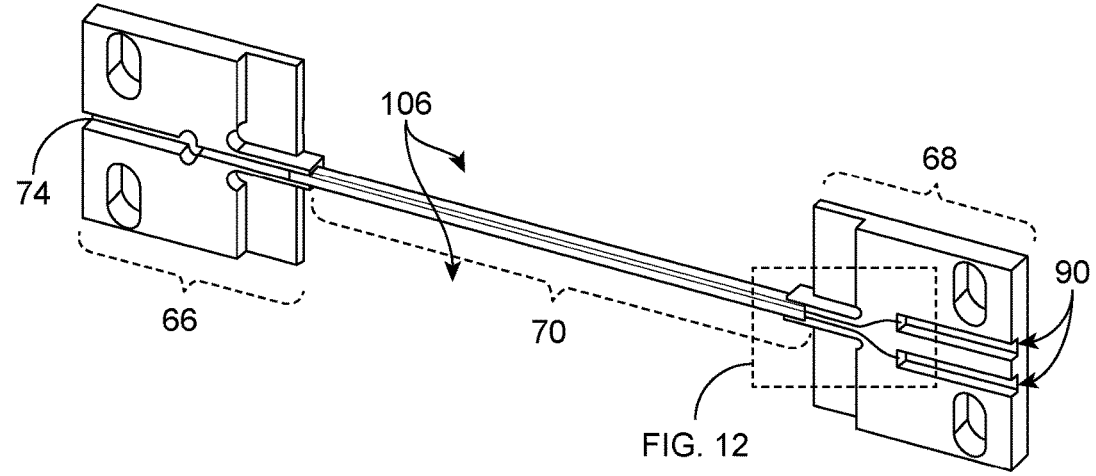
FIG. 11 is a view of the particle isolation device shown in FIG. 10 with some internal details visible.
Figure 12:
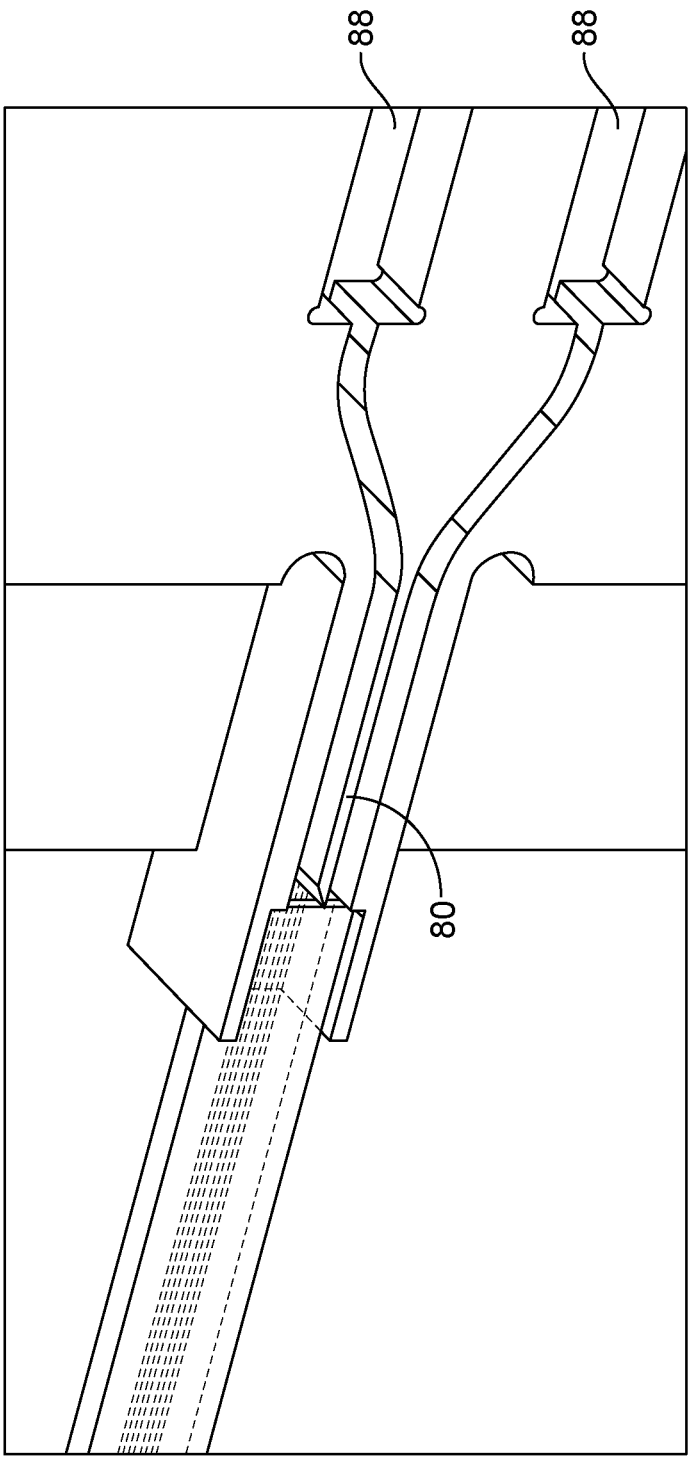
FIG. 12 is a magnified perspective view of a portion of the particle isolation device shown in FIG. 11 indicated by dotted box 12.
Figure 13:
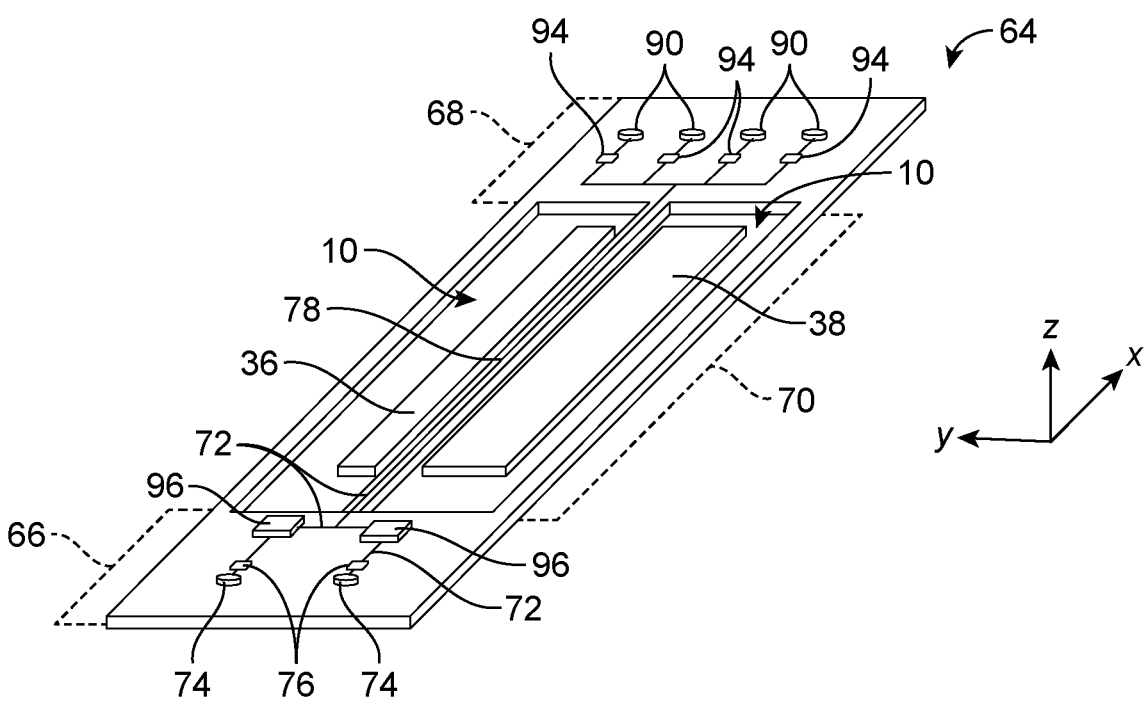
FIG. 13 is a perspective view of an alternative embodiment of a particle isolation device in accordance with the present invention.

Alternatively, the levitation device may comprise an integral configuration, wherein parts of the input portion, the processing portion, and output portion are integrated into a single component such as, for example, a fluidic chip. As shown in FIG. 9, FIG. 10, and FIG. 13, the input manifold, the fluidic channel, and the output manifold may comprise a single integrated fluidic component 64. The levitation device in accordance with this embodiment comprises an integrated fluidic component, an upper magnet and a lower magnet. Integrated fluidic component 64 may comprise a fluidic cartridge (FIG. 10 and FIG. 15) or chip (FIG. 13) that may be a single-use disposable unit.

Referring now to FIG. 9, FIG. 10 and FIG. 13, in a preferred embodiment, levitation device 20 comprises integrated fluidic component 64, support structure 22, upper magnet 36 and lower magnet 38. As shown in FIG. 9, the integrated fluidic component 64, upper magnet 36, and lower magnet 38 may be mounted on support structure 22. Integrated fluidic component 64 comprises an input section 66, an output section 68, and a central processing section 70 that is positioned between input section 66 and output section 68. A fluidics channel structure 72 extends through input section 66, output section 68, and central processing section 70.

Input section 66 includes one or more inlet ports 74 which are in fluid communication with the fluidics channel structure 72. Input section 66 may also include one or more input valves 76 (shown in FIG. 13). Input valves 76 may be included to allow control of the inlet port's communication with the fluidics channel structure 72. In an embodiment input valves 76 are positioned within the channel and positioned adjacent to an inlet port 74. Input section 66 may also include one or more pumps 96 as illustrated in FIG. 13.

The fluidic channel extends from an inlet port 74 through input section 66 and into a processing channel 78, which extends through the central processing section 70. The central processing section 70 together with the upper magnet 36 and lower magnet 38 form the processing portion of the device, which is the functional portion of the device wherein particles of interest are exposed to a magnetic field and thereby isolated. As described more fully below, upper magnet 36 and lower magnet 38 are positioned adjacent the processing channel 78 that extends through processing section 70, such that upper magnet 36 and lower magnet 38 create an asymmetric magnetic force across processing channel 78. For enhanced operability and manufacturability, the central processing section 64 may be offset in the z-axis from the plane of the input section 60 or output section 62, maintaining fluidic connection throughout the device.

Processing channel 78 is preferably an elongated fluidic channel that has sufficient length along the x-axis (shown in FIG. 13) to allow sufficient time for processing a fluid containing the particles of interest based on the residence time required for the particles to closely approach a height equilibrium (along the y-axis) within the processing channel 78, and based on the desired throughput from the system. In accordance with an embodiment, the processing channel is a fluidic channel that has a height of about 200 microns to about 30 mm, about 200 microns to about 20 mm, about 200 microns to about 15 mm, about 200 microns to about 10 mm, about 200 microns to about 5 mm, about 200 microns to about 2 mm, about 200 microns to about 1 mm, about 0.5 mm to about 1 mm, about 0.5 mm to about 2 mm, about 0.5 mm to about 3 mm, about 1 mm to about 2 mm, about 1 mm to about 3 mm, or about 1.5 mm to about 2 mm. In accordance with an embodiment, the processing channel 78 has a length of about 20 mm to about 200 mm, about 20 mm to about 150 mm, about 20 mm to about 100 mm, about 20 mm to about 50 mm, about 40 mm to about 100 mm, about 40 mm to about 90 mm, or about 40 mm to about 80 mm. The processing channel 78 may have any cross sectional geometric configuration and may comprise a cross sectional geometric configuration that is square, rectangular, round or oval. The geometric characteristics of processing channel 78 described herein are equally applicable to the capillary 32, and fluidic channel 34 described above in reference to the component configuration of the present invention.

In accordance with a preferred embodiment, processing channel 78 terminates with one or more channel dividers 80 that serve as a splitter. The device may include a plurality of channel dividers 80 that may comprise vertically spaced substantially horizontal partitions within the terminal portion of processing channel 78, and which define a plurality of vertically spaced compartments 82 along the terminal portion of processing channel 78. Alternatively, channel dividers may also include one or more horizontally spaced substantially vertical partitions 84 that define a plurality of horizontally spaced compartments so as to create an exit grid as illustrated in FIG. 8. The splitter allows collection of various fractions a fluid that is processed by the device, thereby allowing isolated particles to be collected in a given fraction based on the isolated particle's equilibrium position within the fluid.

Figure 14:
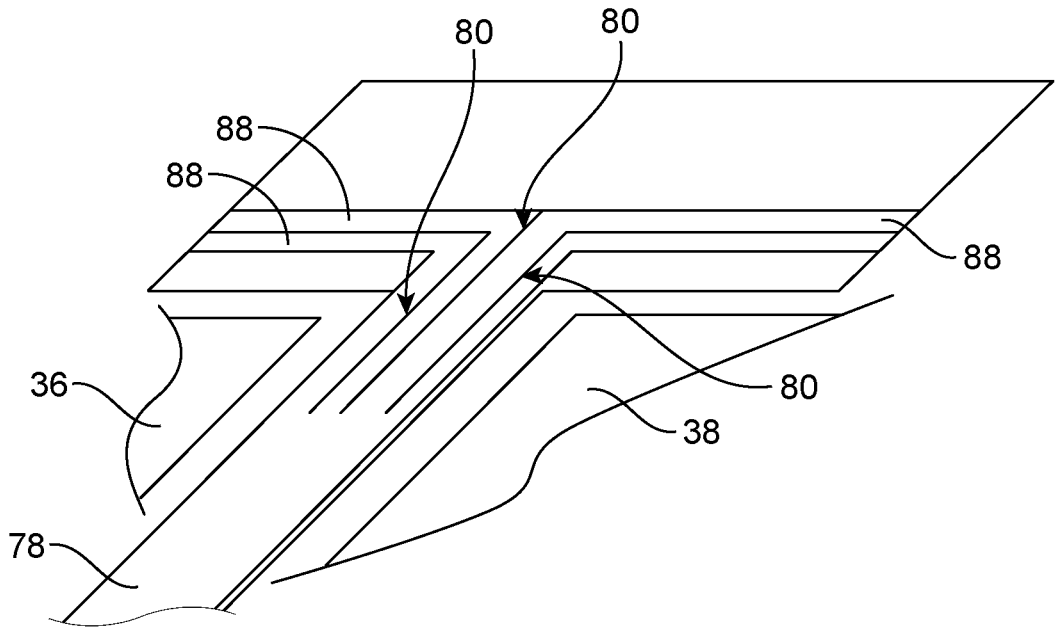
FIG. 14 is a magnified perspective view of the terminal end of processing channel 78 shown in FIG. 13.

The magnetic field which upper magnet 36 and lower magnet 38 create along x-axis of processing channel 78 is strongest at the center point along the x-axis. As a processing fluid moves along the processing channel 78 towards the terminal portion of processing channel 78, the magnetic field can begin to attenuate, and the orientation can also vary. As the fluid path passes through this more spatially-variable magnetic field, there may be a tendency for the isolated particles to begin to migrate from their equilibrium height. This tendency can be exacerbated once the particles move beyond the magnets. Accordingly, in accordance with a preferred embodiment, channel dividers 80 extend from the terminal end of processing channel 78 back into the processing channel 78, and extend back to at least a portion of the processing channel that is between the terminal portion of upper magnet 36 and the terminal portion of lower magnet 38, as illustrated in FIG. 14, which is a magnified perspective view of the terminal end of processing channel 78 shown in FIG. 13. This configuration can allow permanent separation of the isolated particles before the spatial variation of the magnetic field results in a degradation of the isolation. The level of magnetic field attenuation can be a function of the distance between the upper magnet and lower magnet. Therefore, in accordance with a preferred embodiment, channel dividers 80 overlap with the terminal portion of upper magnet 36 and the terminal portion of lower magnet 38 along the x-axis of the device by a distance that is at least about 10% to about 300% of the size of the gap between the upper and lower magnets, or about 20% to about 280%, about 30% to about 260%, about 40% to about 240%, about 50% to about 220%, about 60% to about 200%, about 70% to about 180%, or about 80% to about 160%.

The channel divider(s) defines a plurality of effluent fluidic channels 88 (See, FIG. 9, FIG. 11, FIG. 12 and FIG. 14). In accordance with an embodiment the levitation device of the present invention includes a splitter that defines 2, 3, 4, 5, 6, 7, 8, 9 or 10 effluent fluidic channels. In accordance with an embodiment the levitation device of the present invention includes a splitter that defines at least 2, at least 3, at least 4, at least 5, at least 6, at least 7, at least 8, at least 9, or at least 10 effluent fluidic channels. In accordance with an embodiment the levitation device of the present invention includes a splitter that defines 2 to 4, 5 to 7, or 8 to 10 effluent fluidic channels. The splitter described herein, and the various resulting effluent fluidic channels, may be incorporated into the capillary 32 and fluidic channel 34 described above in reference to the component configuration of the present invention.

The plurality of effluent fluidic channels extend from processing channel 78 to a corresponding plurality of outlet ports 90. The plurality of effluent fluidic channels may include fluidic flow controllers, such as output valves 94, which control the amount of flow from processing channel 78 through the respective effluent channels to the respective outlet ports.

Figures 15, 16:
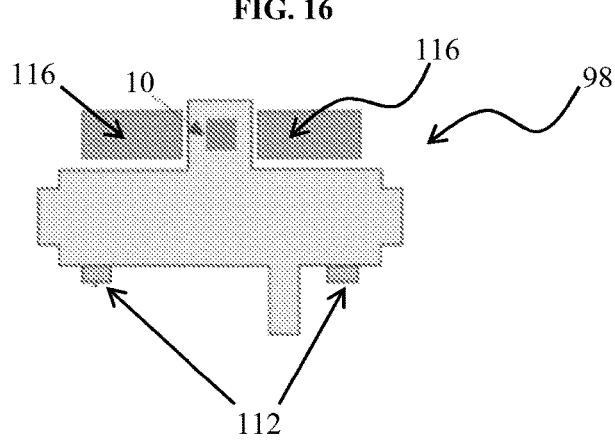
FIG. 15 is a perspective view of an alternative embodiment of a particle isolation device in accordance with the present invention.
FIG. 16 is a cross-sectional view of the device shown in FIG. 15 taken along line B-B and with magnets 116 shown.

An alternative embodiment of a fluidic cartridge 98 in accordance with the present invention is shown in FIG. 15 and FIG. 16. FIG. 16 is a cross-sectional view of the device shown in FIG. 15 taken along line B-B. In accordance with this embodiment, there is included an inlet port 100 in fluidic communication with an internal fluidics structure 102 which includes a fluidics channel processing segment 104. Fluidic cartridge 98 also includes two recessed portions 106 that are adjacent fluidics channel processing segment 104 (shown in FIG. 15), and are adapted to receive magnets 116 (shown in FIG. 16). The fluidics structure 102 includes a splitter 108, which splits the fluidics channel processing segment 104 into two effluent channels 110 each of which leads to an outlet ports 112. Fluidic cartridge 98 also includes a visualization window 114 positioned adjacent to fluidics channel processing segment 104. Visualization window 114 may comprise a substantially clear window that is adapted to allow an optical device such as the device shown in FIG. 21, to facilitate observation and/or video recording of the particles as they are exposed to the magnetic field in fluidics channel processing segment 104. Visualization window 114 may also comprise a sufficiently transparent section of channel such that visualization of the contents is achievable.

C. Magnet Configuration

In accordance with a preferred embodiment, magnets are positioned above and below capillary 32 (FIG. 5 and FIG. 6) or central processing section 70 (FIG. 9 and FIG. 13), and are positioned in a magnetic repelling orientation relative to one another such that they create a magnetic field vertically across fluidic channel 34, wherein the magnetic field within fluidic channel 34 is asymmetric at least along the vertical direction. In accordance with an embodiment, the magnets are centered with the fluidic processing channel along the length thereof (i.e. along the x-axis shown in FIG. 13).

In accordance with a preferred embodiment, at least one of the upper magnet 36 or the lower magnet 38 is configured to create a greater magnetic field on fluidic channel 34 than the other magnet, thereby resulting in an asymmetric magnetic force within fluidic channel 34, e.g. as illustrated in FIG. 3B. This greater force can be achieved by either: (1) using a larger magnet on one side of the fluidic channel 34 (as illustrated by larger upper magnet 36 in FIG. 5); (2) including multiple magnets on one side of the fluidic channel 34 (in an attractive, rather than repelling, arrangement relative to one another) (as illustrated by lower magnets 40 in FIG. 6); (3) by positioning one of the two magnets closer to fluidic channel 34 than the other magnet (as illustrated in FIG. 6); or (4) some combination thereof.

In accordance with an embodiment, one or both of the upper magnet 36, the lower magnet 38, or lower magnets 40 are movably mounted within the system to allow controlled adjustment of the vertical position of the magnet relative to fluidic channel 34, and to allow adjustment of the asymmetry of the magnetic field. In accordance with an embodiment, the levitation device includes an upper magnet or a lower magnet that comprises a plurality of magnets that are movably mounted such that number of magnets that are engaged (i.e., actively creating a magnetic field across the processing section of the fluidic channel) may be controlled, thereby controlling the magnitude and gradient profiles of the magnetic field. Control over the magnetic field as a function of time can permit more complex protocols which can be changed at any time during an experiment or assay. Among other advantages over a static system, this can permit: more flexible partitioning of samples; higher resolution in the separation of particles; more flexible methods to purge, prime and treat the fluidic paths; and feedback to optimize or change the separation parameters at the time of running an experiment or assay.

In accordance with an embodiment, upper magnet 36 and lower magnet 38 comprise elongated rectangular magnets (preferably bar magnets), whose dimensions range from a height (y-axis from FIG. 13 (vertical axis)) of about 2 mm to about 25 mm, a width (x-axis from FIG. 13) of about 30 mm to about 80 mm, and a depth (z-axis from FIG. 13) of about 0.5 mm to about 7 mm. Preferably, upper magnet 36 and lower magnet 38 have dimensions ranging from a height (y-axis from FIG. 13) of about 4 mm to about 20 mm, a width (x-axis from FIG. 13) of about 40 mm to about 60 mm, and a depth (z-axis from FIG. 13) of about 1 mm to about 3 mm. The preferred magnet sizes described herein may be achieved by one magnet or by combining multiple magnets. In accordance with an embodiment, depth and the width of upper magnet 36 and lower magnet 38 are substantially the same. In accordance with an embodiment, the height of upper magnet 36 is at least about 25%, 50%, 75%, 100%, 125%, 150%, 175%, 200%, 225%, 250%, 275%, 300%, 325%, 350%, 375%, 400%, 425%, 450%, 475%, or 500% larger than the height of lower magnet 38. In accordance with an embodiment, the height of upper magnet 36 is about 25% to about 100%, about 100% to about 200%, about 200% to about 300%, about 300% to about 400%, about 400% to about 500%, or about 500% to about 600% larger than the height of lower magnet 38. In accordance with an embodiment, the height of lower magnet 38 is at least about 25%, 50%, 75%, 100%, 125%, 150%, 175%, 200%, 225%, 250%, 275%, 300%, 325%, 350%, 375%, 400%, 425%, 450%, 475%, or 500% larger than the height of upper magnet 36. In accordance with an embodiment, the height of lower magnet 38 is about 25% to about 100%, about 100% to about 200%, about 200% to about 300%, about 300% to about 400%, about 400% to about 500%, or about 500% to about 600% larger than the height of upper magnet 36.

In accordance with an embodiment, the distance between the upper and lower magnets and the fluidic channel 34, capillary 32 or central processing section 70 along the vertical axis is at least about 1 micron, 10 microns, 50 microns, or 100 microns and/or is no greater than about 500 microns, 1 mm, 2 mm, 3 mm, 4 mm, or 5 mm. In accordance with an embodiment, the distance between either of the magnets and the fluidic processing channel is between about 1 micron to about 5 mm along the vertical axis, and preferably about 10 microns to about 2 mm.

In accordance with an embodiment, the vertical distance between the upper magnet and the fluidic processing channel is at least about 25%, 50%, 75%, 100%, 125%, 150%, 175%, 200%, 225%, 250%, 275%, 300%, 325%, 350%, 375%, 400%, 425%, 450%, 475%, or 500% greater than the vertical distance between lower magnet and the fluidic processing channel. In accordance with an embodiment, the vertical distance between the upper magnet and the fluidic processing channel is at least about 25% to about 100%, about 100% to about 200%, about 200% to about 300%, about 300% to about 400%, about 400% to about 500%, or about 500% to about 600% greater than the vertical distance between the lower magnet and the fluidic processing channel.

In accordance with an embodiment, the vertical distance between the lower magnet and the fluidic processing channel is at least about 25%, 50%, 75%, 100%, 125%, 150%, 175%, 200%, 225%, 250%, 275%, 300%, 325%, 350%, 375%, 400%, 425%, 450%, 475%, or 500% greater than the vertical distance between upper magnet and the fluidic processing channel. In accordance with an embodiment, the vertical distance between the lower magnet and the fluidic processing channel is at least about 25% to about 100%, about 100% to about 200%, about 200% to about 300%, about 300% to about 400%, about 400% to about 500%, or about 500% to about 600% greater than the vertical distance between the upper magnet and the fluidic processing channel.

In accordance with an embodiment, upper magnet 36 and lower magnet 38 are permanent magnets or electromagnets. In accordance with an embodiment, the maximum energy product of upper magnet 36 and lower magnet 38 ranges from about 1 Mega-Gauss Oersted to about 1000 Mega-Gauss Oersted, and more preferably ranges from about Mega-Gauss Oersted to about Mega-Gauss Oersted. In accordance with an embodiment, the surface field strength of upper and lower magnets ranges from about 0.1 Tesla to about 100 Tesla, and more preferably ranges from about 1 Tesla to about 10 Tesla. In accordance with an embodiment, the remanence of upper and lower magnets ranges from about 0.5 Tesla to about 5 Tesla, and more preferably ranges from about 1 Tesla to about 3 Tesla.

In accordance with a preferred embodiment, upper magnet 36 and lower magnet 38 are made from a material comprising neodymium alloys with iron and boron, neodymium, neodymium alloys with iron, samarium-cobalt, other alloys of rare earth elements with iron, alloys of rare earth alloys with nickel, ferrite, alloys of aluminum with iron, or combinations thereof. In accordance with an embodiment, upper magnet 36 and lower magnet 38 are made from the same material or are made from different materials.

In accordance with a preferred embodiment, an asymmetric magnetic field is achieved by using a stronger magnetic material on one side of a fluidic channel and a weaker magnetic material on the opposite side of the fluidic channel. In accordance with such embodiment, upper magnet 36 and lower magnet 38 may be substantially the same size, but still yield an asymmetric magnetic force across fluidic channel 34. In accordance with such embodiment, upper magnet 36 may comprise neodymium, lower magnet 38 may comprise samarium-cobalt, and wherein both magnets are substantially the same size. Alternatively, upper magnet 36 may comprise samarium-cobalt, lower magnet 38 may comprise neodymium, and wherein both magnets are substantially the same size.

In accordance with an embodiment, alternative magnet configurations may be used. Referring to FIG. 17A, the device in accordance with the present invention may include multiple upper magnets and multiple lower magnet positioned around a fluidic channel. Upper magnets may include an anterior upper magnet 118, a central upper magnet 120, and a posterior upper magnet 122. Lower magnets may include an anterior lower magnet 126, a central lower magnet 128, and a posterior lower magnet 130. As illustrated in FIG. 17A, references to the magnets as anterior, posterior, and central refers to the magnets' positions along the z-axis relative to the fluidic channel 124, and references to the magnets as upper and lower refers to the magnets' positions along the y-axis relative to the fluidic channel 124. Arrows 132 indicate the orientation of the magnetic fields for magnets 118, 120, 122, 126, 128, and 130, and as illustrated, the upper and lower magnets are positioned in a magnetic repelling orientation.

In accordance with another embodiment, further alternative magnet configurations may be used. Referring to FIG. 17B, the device in accordance with the present invention may include multiple upper magnets and multiple lower magnet positioned around a fluidic channel. Upper magnets may include an anterior upper magnet 140, a central upper magnet 120, and a posterior upper magnet 146. Lower magnets may include an anterior lower magnet 142, a central lower magnet 128, and a posterior lower magnet 144. As illustrated in FIG. 17B, references to the magnets as anterior, posterior, and central refers to the magnets' positions along the z-axis relative to the fluidic channel 124, and references to the magnets as upper and lower refers to the magnets' positions along the y-axis relative to the fluidic channel 124. Arrows 132 indicate the orientation of the magnetic fields for magnets 140, 120, 146, 142, 128, and 144, and as illustrated, the three upper magnets are in an anti-parallel configuration and the three lower magnets are in an anti-parallel configuration, and the central upper and central lower magnets are positioned in a magnetic repelling orientation.

Referring to FIG. 18, another magnet configuration is illustrated. In accordance with this embodiment, the device may include an anterior upper magnet 334, a posterior upper magnet 336, an anterior lower magnet 338, and a posterior lower magnet 340, wherein the magnets are positioned around fluidic channel 342. Arrows 344 indicate the orientation of the magnetic fields for the magnets, and as illustrated anterior upper magnet 334 and posterior lower magnet 340 are positioned in a magnetic repelling orientation, and posterior upper magnet 336 and anterior lower magnet 338 are positioned in a magnetic repelling orientation. The anterior and posterior magnets modify the field profile within the channel, enhancing performance.

In accordance with the embodiments illustrated in FIG. 17A, FIG. 17B, and FIG. 18, the magnetic field exerted on fluidic channels 124 and 142 may be asymmetric, and preferably asymmetric within the x-y plane. The asymmetry may be achieved in accordance with the methods described hereinabove, including by adjusting the positions of one or more magnets relative to the fluidic channel, and/or by using stronger magnets (larger magnets or different magnetic materials) either on: (1) the upper side relative to the magnets on the lower side, (2) the lower side relative to the magnets on the upper side, (3) the anterior side relative to the magnets on the posterior side; and/or (4) the posterior side relative to the magnets on the anterior side. In accordance with embodiments having magnetic configurations shown in FIG. 17A or FIG. 17B, the central lower magnet is stronger than central upper magnet, and/or is stronger than either or both the anterior lower magnet and the posterior lower magnet. In accordance with embodiments having magnetic configurations shown in FIG. 17A or FIG. 17B, the central upper magnet is stronger than central lower magnet, and/or is stronger than either or both the anterior upper magnet and the posterior upper magnet.

D. Serial and Parallel Configuration

In accordance with an embodiment, the isolation device or levitation device of the present invention may comprise a plurality of processing segments interconnected in series and/or in parallel. A device with such multiple interconnected processing segment can enhance the device's ability to separate particles with higher specificity and enhance the device's ability to divide the volume of the fluid itself at a wide range of ratios. Either a parallel or a serial configuration may be used to increase the throughput of the device in the sense that an increased quantity of sample may be processed in a given period of time.

Figure 19:
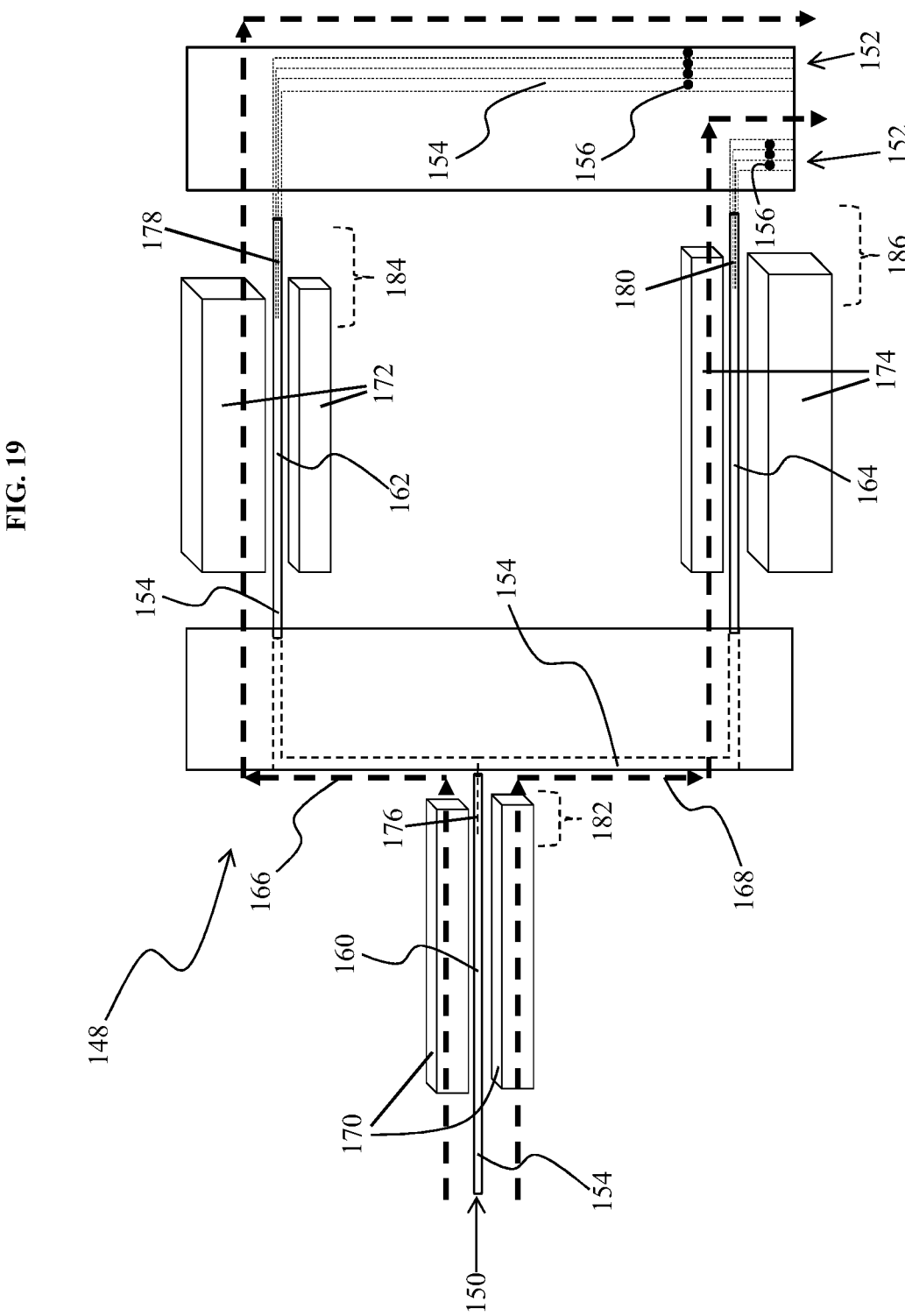
FIG. 19 is a perspective view of an alternative embodiment of a particle isolation device in accordance with the present invention.
Figure 20:
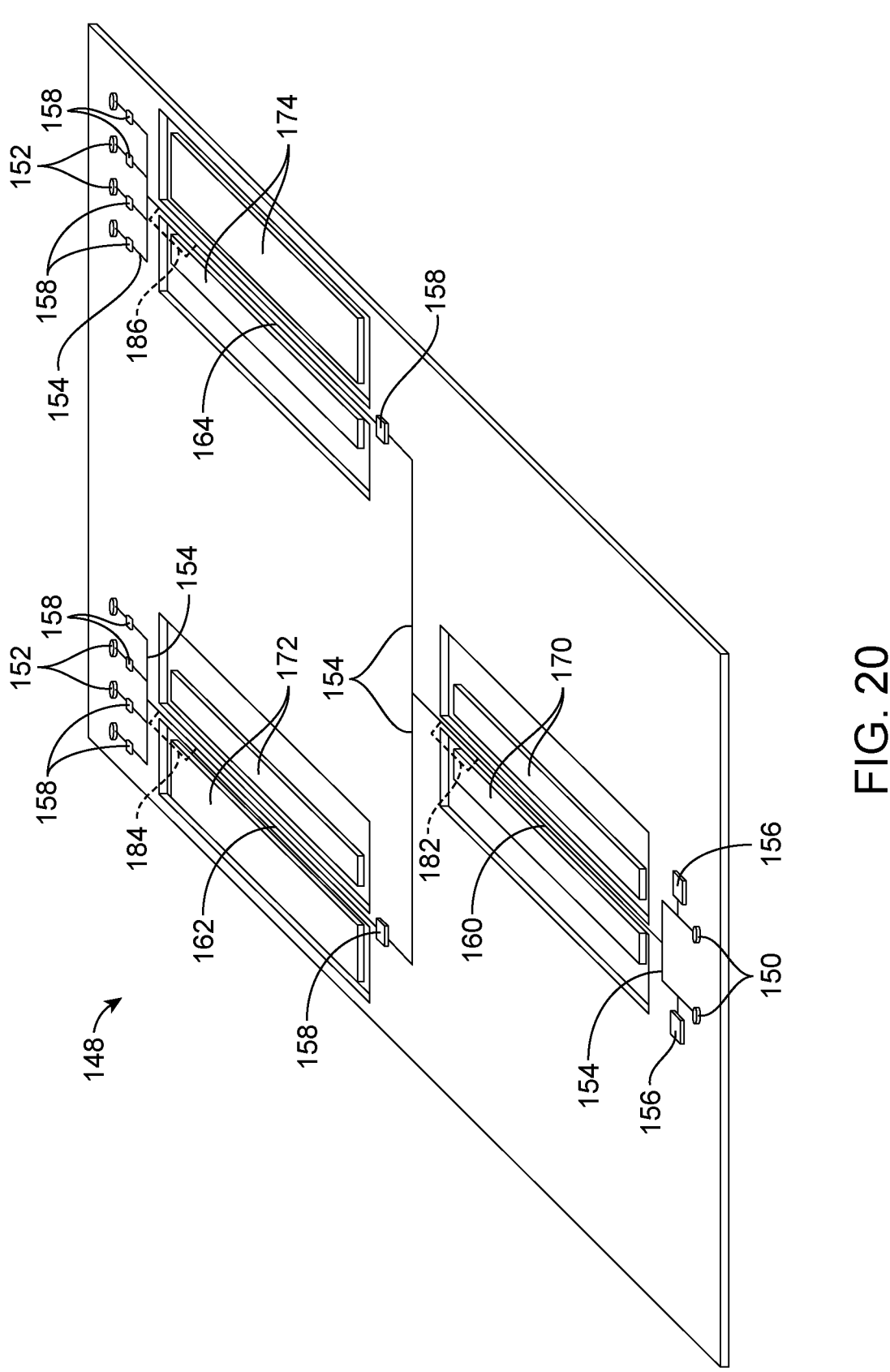
FIG. 20 is a perspective view of an alternative embodiment of a particle isolation device in accordance with the present invention.

Referring to FIG. 19 and FIG. 20, a particle isolation device 148 is shown. The device 148 includes a fluidic channel structure extending therethrough. The fluidic channel structure includes at least one input port 150 and at least two output ports 152 interconnected by a fluidic channel structure comprising a series of fluidic channels 154, pumps 156, and valves 158. The series of fluidic channels include a first substantially linear portion 160, a second substantially linear portion 162, and a third substantially linear portion 164. A first processing pathway indicated by upper pathway dotted line 166 (FIG. 19) extends from an inlet (input) port 150 to said first substantially linear portion 160 and from said first substantially linear portion 160 to said second substantially linear portion 162 and from said second substantially linear portion 162 to an outlet (output) port 152. A second processing pathway indicated by lower pathway dotted line 168 (FIG. 19) extends from an inlet port 150 to said first substantially linear portion 160 and from said first substantially linear portion 160 to said third substantially linear portion 164 and from said third substantially linear portion 164 to an outlet (output) port 152. It should be readily understood that the substantially linear portions 160, 162, and 164 can be designed to be linear primarily for ease of manufacturing and operability. In general, they may be curved provided that the magnetic fields along their length are suitable for levitation to occur.

Device 148 further comprises a first pair of magnetic components 170, a second pair of magnetic components 172, and a third pair of magnetic components 174 that are substantially vertically positioned on opposite sides of the first substantially linear portion 160, the second substantially linear portion 162, and the third substantially linear portion 164 of the fluidic channel structure, respectively. In accordance with an embodiment, an isolation device or levitation device having a plurality of processing segments interconnected in series and/or in parallel is provided wherein each processing segment includes a pair of magnetic components and at least one of said pair of magnetic components is configured to exert an asymmetric magnetic force within its adjacent substantially linear portion of the fluidic channel. In accordance with this embodiment, the asymmetry of the magnetic force may be achieved in any manner described herein above.

In accordance with the embodiments shown in FIG. 19 and FIG. 20, the first pair of magnetic components 170 comprise identical magnets equally spaced from the first substantially linear portion 160 of the fluidic channel, the second pair of magnetic components 172 comprise an upper magnet that is larger than the lower magnet with both magnets being equally spaced from the second substantially linear portion 162 of the fluidic channel, and the third pair of magnetic components 174 comprise an upper magnet that is smaller than the lower magnet with both magnets being equally spaced from the third substantially linear portion 164 of the fluidic channel. In accordance with this embodiment, the magnetic neutral line within the first substantially linear portion 160 of the fluidic channel is located along the vertical center of the fluidic channel, the magnetic neutral line within the second substantially linear portion 162 of the fluidic channel is located below the vertical center of the fluidic channel, and the magnetic neutral line within the third substantially linear portion 164 of the fluidic channel is located above the vertical center of the fluidic channel.

Device 148 includes a first splitter 176 positioned at the trailing end 182 of the first substantially linear portion 160, a second splitter 178 positioned at the trailing end 184 of the second substantially linear portion 162, and a third splitter 180 positioned at the trailing end 186 of the third substantially linear portion 164. In accordance with an embodiment, first splitter, second splitter, and third splitter split the channel into two or more channels. In accordance with an embodiment, first splitter splits the channel into two channels, where by one of such split channels leads to the second substantially linear portion 162 and the second of such split channels leads to the third substantially linear portion 164. Alternatively, such embodiment may include a three-way splitter as the first splitter, with the third channel leading to a non-processed waste effluent.

In accordance with an embodiment, the first pair of magnetic components 170 is configured to exert a magnetic force along the fluidic channel extending within the first substantially linear portion 160 wherein such magnetic force is vertically symmetrical about the vertical centerline of such fluidic channel. In accordance with this embodiment, the second pair of magnetic components 172 is configured to exert a magnetic force along the fluidic channel extending within the second substantially linear portion 162 wherein such magnetic force is vertically asymmetrical about the vertical centerline of such fluidic channel and is biased downward. Also, in accordance with this embodiment, the third pair of magnetic components 174 is configured to exert a magnetic force along the fluidic channel extending within the third substantially linear portion 164 wherein such magnetic force is vertically asymmetrical about the vertical centerline of such fluidic channel and is biased upward. In accordance with this embodiment, the asymmetry of the magnetic forces may be achieved in any manner described herein above. In accordance with the embodiments illustrated in FIG. 19 and FIG. 20, the asymmetry is achieved within the fluidic channel extending within the second substantially linear portion 162 by having an upper magnet 36 that is larger than lower magnet 38, and the asymmetry is achieved within the fluidic channel extending within the third substantially linear portion 164 by having an upper magnet 36 that is smaller than lower magnet 38.

Figure 25:
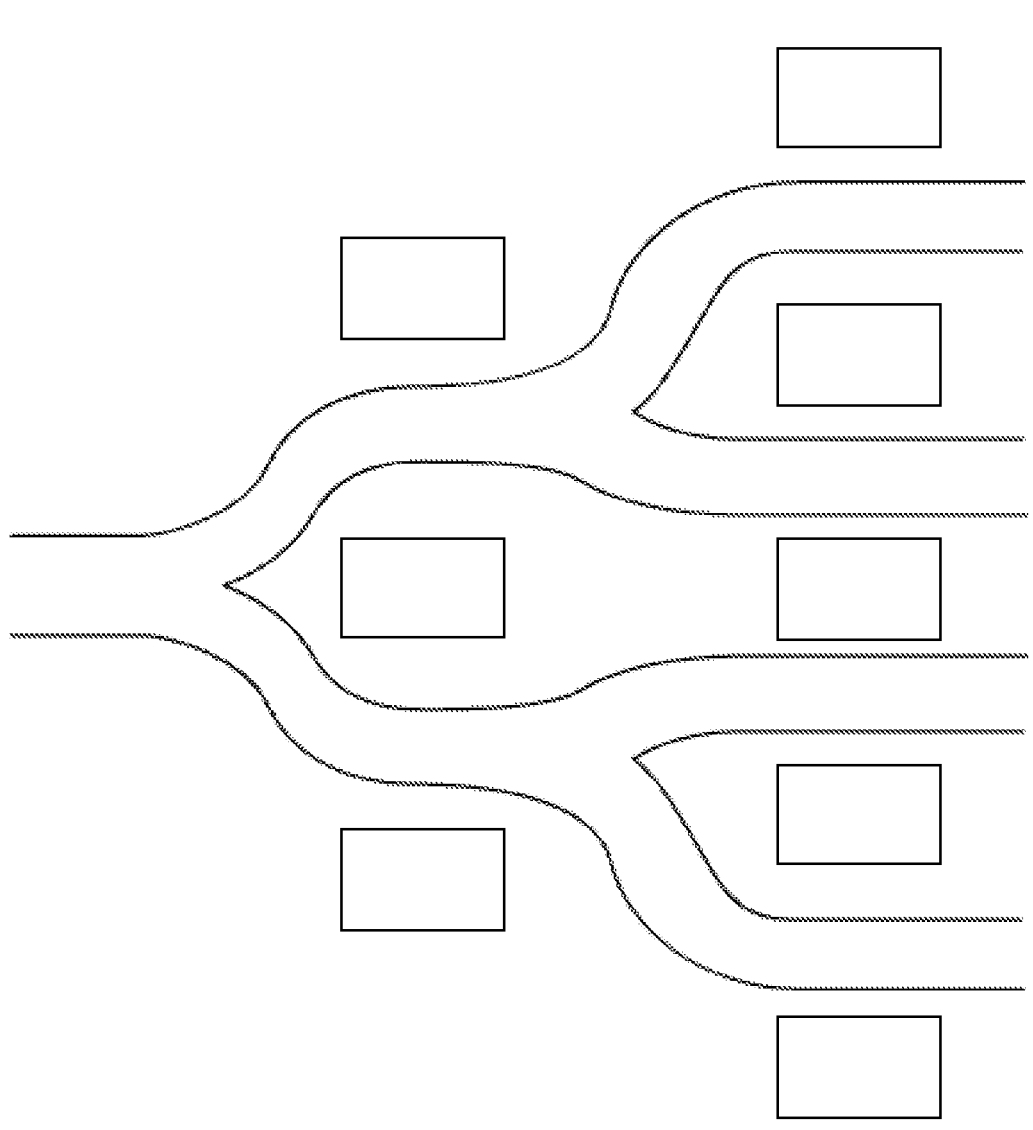
FIG. 25 is a conceptual schematic of a branched parallel channel device with shared central magnets.
Figures 26, 27:
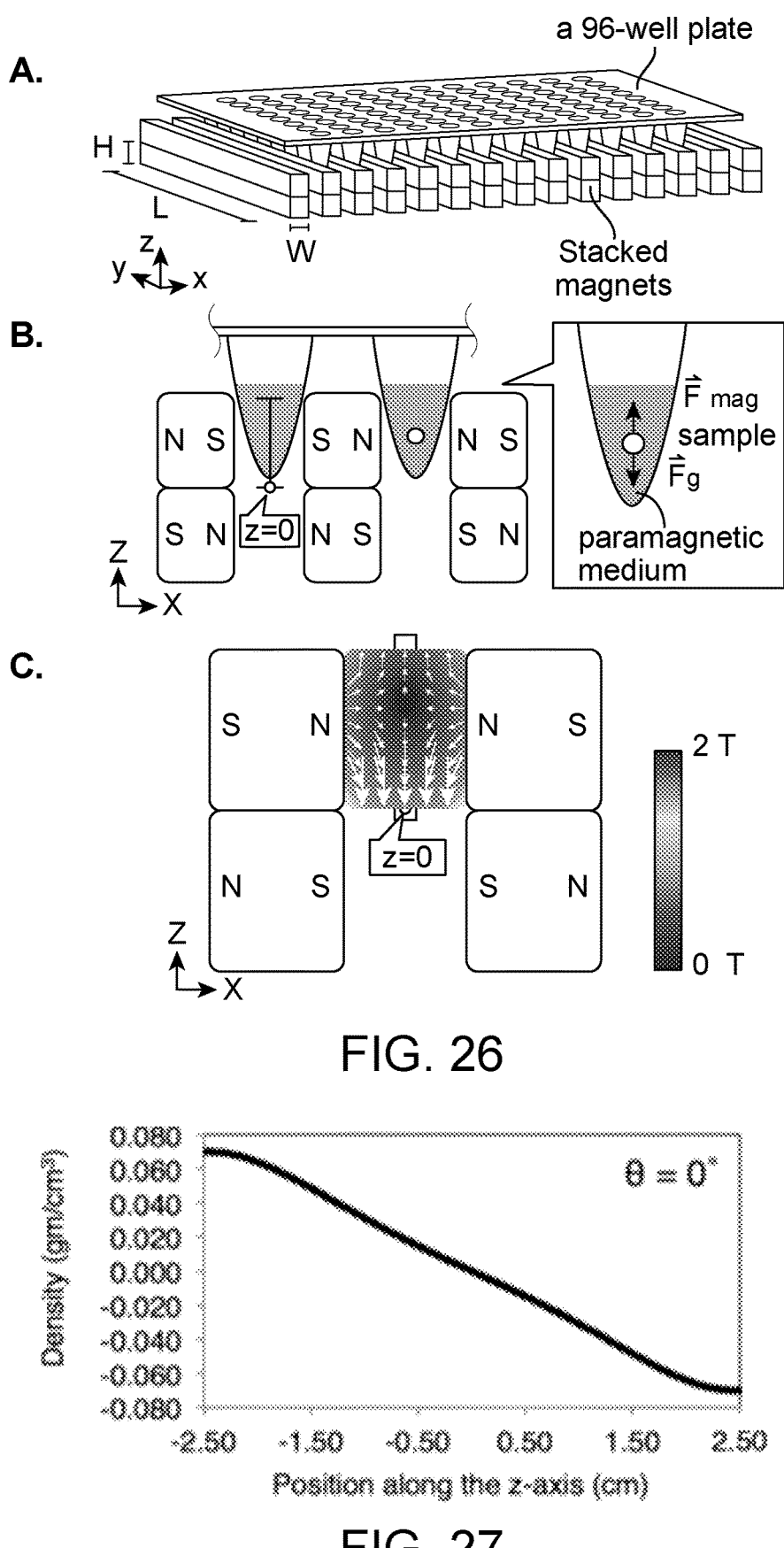
FIG. 26 is a conceptual schematic of a well-assay particle separation device that shares magnets between neighboring wells.
FIG. 27 illustrates a difference in particle density (gm/$cm^3$) vs. position along the z-axis (cm).

In some embodiments, the particle isolation device may comprise a series of one or more sets of parallel channels, giving the device a branching structure, as shown in FIG. 25. In some embodiments of a branched particle isolation device, the parallel fluidic channels may share a common central magnet. Optionally, this embodiment may contain a series of shared central magnets between the parallel channels. The magnets may be positioned to generate a magnetic field that alters the nature of the achieved particle separation as desired. The particle isolation device can comprise at least 1, 2, 3, 4, 5, 6, 7, 8, 9, 10, or more magnets. In some embodiments, the particle isolation device may comprise one or more wells for hydrostatic separation of particle mixtures. In some embodiments, neighboring wells or channels will share one or more common magnets. Optionally, multiple magnets may be stacked to create a shaped magnetic field that creates a focused centerline in a well, as shown in FIG. 26. The fields defining this centerline can serve as a focusing mechanism that may allow particles to become separated in groups, e.g., tight groups along the centerline of the well, easing detection. The magnets surrounding the wells or channels may be horizontally arranged to spread the particle equilibrium positions out. This may commensurately decrease the dynamic range and may increase the time taken to equilibrate. The stacking of multiple magnets adjacent to each well may modify the shape of the field gradients in a way that sharpens the field gradient to improve separation efficiency. The stacked magnet configuration may compress the magnetic field lines to improve performance. In some cases, a sample can circulate through each well. In some cases, using this in a step-and-hold style can allow for batched analysis, which can be useful for dilute samples. FIG. 27 illustrates a difference in density ($gm/cm^3$) vs. position along the z-axis (cm).

Device 148 may also include one or more pumps 156 configured to drive fluid from input port 150 through the fluidic channel and out an output port 152. Device 148 may also include one or more valves 158 to allow control of the amount of fluid that flows along the various pathways included in the fluidic channel structure.

E. Pumps

In accordance with the present invention, the device may include one or more pumps to drive fluid through the system. "Pump" is used to refer to any device which applies a difference in pressure between different locations in the channel structure. Pumps may be placed on either the inlet side of the system (pushing fluid toward the outlet(s)), or on the outlets (pulling liquid from the inlet(s)), or a combination of both. The difference in pressure may be positive or negative. The pressure difference may be applied in common across multiple outlets or inlets, or may by arranged such that each outlet or inlet has a directly-applied pressure difference. The pumps may variable to allow control of the applied pressure difference. Pump types include, but are not limited to: positive displacement pumps such as syringe pumps; peristaltic pumps; diaphragm pumps; regulated static pressure sources; gravitationally-controlled pressure sources such as elevated or lowered volumes of liquid; and manual sources of pressure such as plastic or foil blisters.

In some embodiments, a pump may be included on inlet line(s) to generally drive fluid through the channel structure, and also included on certain outlet lines (but not all) to selectively drive more fluid through certain outlet lines. For example, pumps may be included on one or more outlet lines associated with the equilibrium levitation height or heights of one or more particles of interest. In addition, all outlet lines may include a variable pump that may be activated or deactivated based on the anticipated equilibrium levitation height or heights of one or more particles of interest. Similarly, external pumps may be controlled to provide a variable pressure differential.

F. Additional Device Components

Figure 21:
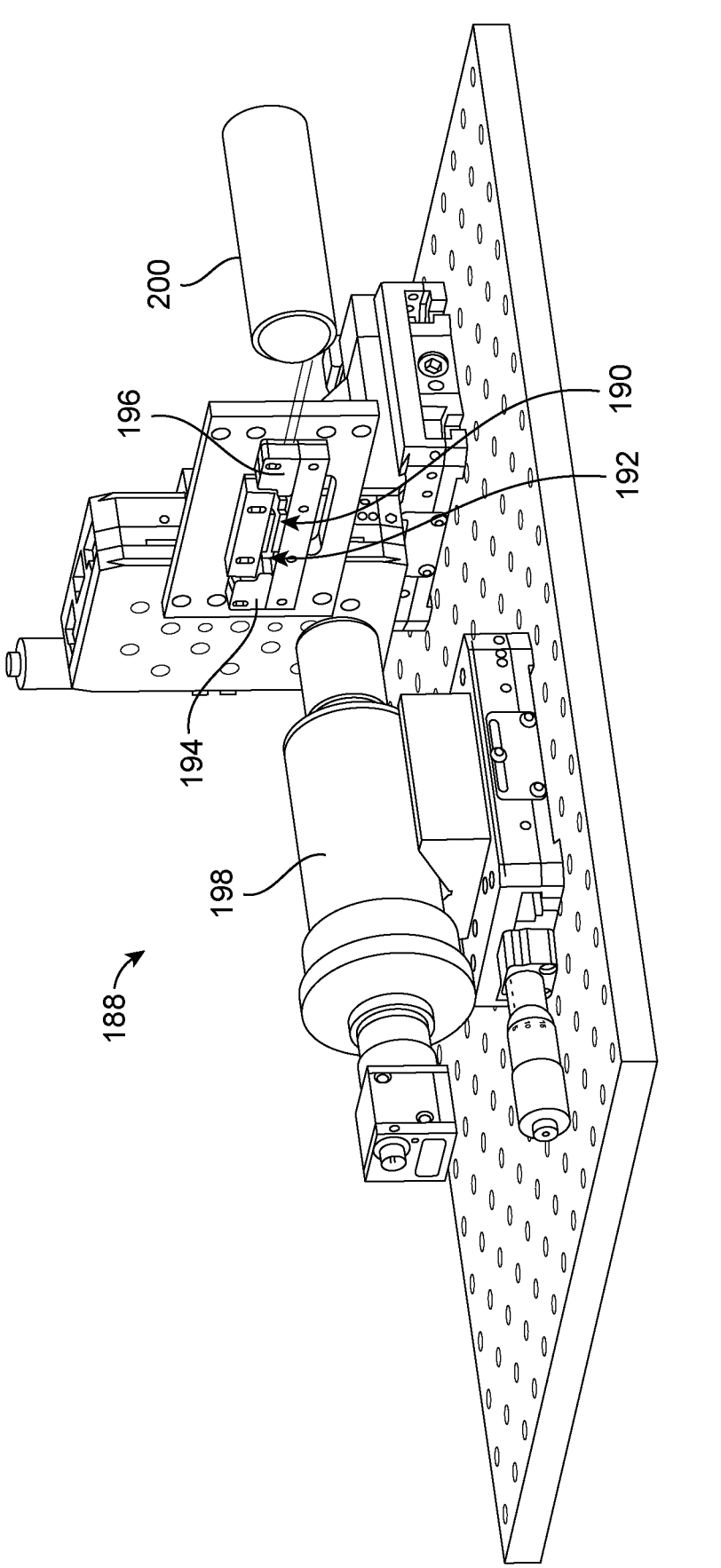
FIG. 21 is a perspective view of an alternative embodiment of a particle isolation device in accordance with the present invention.

The levitation device or particle isolation device in accordance with the present invention may also include additional components as illustrated in FIG. 21. In accordance with this embodiment, the particle isolation device 188 includes input manifold 194, output manifold 196, processing channel 192, and a pair of magnets 190. Magnets 190 are positioned above and below processing channel 192 and are configured to exert a magnetic field across processing channel 192. Magnets 190 and processing channel 192 may be configured in accordance with any of the magnet/channel configurations and embodiment described hereinabove. Device 188 further comprises a visualization component 198 and an illumination component 200. Visualization component 198 may comprise any device which enables or enhances the ability to view in real time and/or to record particles as they pass through processing channel 192, thereby enabling observation and/or measurement of the isolation of the particles, including the extent of particle isolation and/or the rate of particle isolation. Visualization may also include analysis of the size, shape, or other characteristics of the particles and/or other components of the sample. In accordance with an embodiment, the material used to surround and thereby define processing channel 192 is clear or transparent along at least a segment of the processing channel 192 to facilitate observation of particles passing therethrough.

In an embodiment, the device includes two clear or transparent segments, with each on opposite sides of channel 192. In accordance with this embodiment, the visualization component 198 is positioned on one side and focused one of said clear or transparent segments, and an illumination component 200 positioned on the opposite side and focused the second of said clear or transparent segments. The illumination component 200 is configured to provide sufficient light to facilitate the visualization of the particles within processing channel 192 by the visualization component 198.

Figures 22A, 22B:
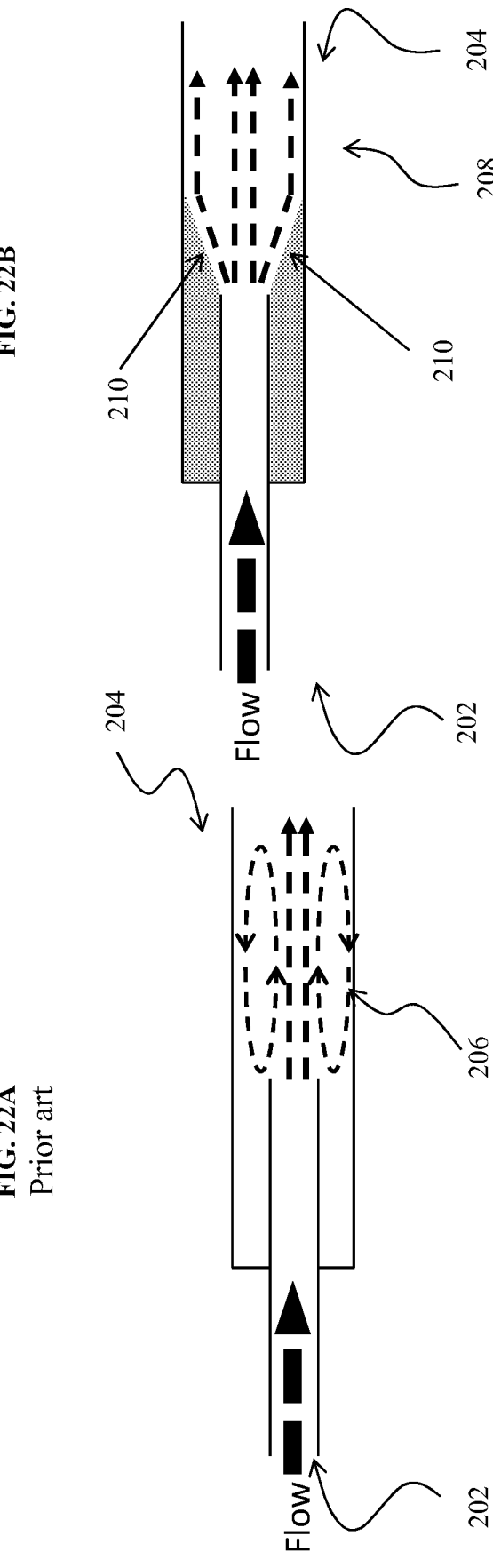
FIGS. 22A and 22B are cross sectional views of a prior art fluidic channel (FIG. 22A) and a fluidic channel (FIG. 22B) in accordance with an embodiment of the present invention.

In an embodiment the particle isolation device of the present invention also includes a tapered entry port. As illustrated in FIG. 22A, prior art fluidics devices include a fluid input port 202 leading to fluidics channel 204. Dotted lines 206 in FIG. 22A illustrate the fluid flow vectors in prior art non-tapered entry ports. In such devices, vortexes are created at the entry of the fluidics channel 204. These vortexes may reduce the efficiency or rate of processing a sample, by providing locations where cells or other particles can be trapped in a circulating path, rather than flowing through the device. Vortex flow may also induce shear stresses on particles such as cells. In accordance with an embodiment of the present invention, as illustrated in FIG. 22B, the fluid input port 202 includes a tapered transition 210 into the fluidics channel 204. The tapered transition substantially eliminates vortexes, and results in smooth laminar fluid flow into fluidics channel 204 as represented by the dotted vector lines 208.

Further additional components may include: a receptacle for holding one or more outlet collection tubes; a receptacle for holding one or more input tubes; a component comprising a receptacle for one or more tubes which is temperature-controlled, for example a cold plate which stores one or more outlet tubes at a temperature close to 4 degrees centigrade; or a microplate holder, which may include positioning means to couple inlets or outlets to wells in the microplate. The device may also be integrated with a microprocessor or computer that is programed to record, analyze, and/or control the fluid and/or particle flow and separation through the device.

IV. Methods of Isolating Particles

In accordance with the method of the present invention, particles may be isolated using the device described hereinabove. Numerous applications require the isolation of particles, including applications requiring the separation of like particles from other particles, identification of particles, and the treatment or otherwise manipulation of particles. Such applications include, but are not limited to, separating live and dead cells, isolation and/or treatment of circulating tumor cells, emulsion PCR enrichment, isolation of circulating fetal cells, production of plasma such as platelet rich plasma, isolating sperm for specific traits such as gender selection, bacterial load testing, antibiotic resistance testing, identification of sepsis or blood contamination, immune cell isolation, compound screening, exosome separation, or extracellular vesicles separation. The particle isolation methods of the present invention may be utilized in any of these applications.

In accordance with the method of the present invention, a substance containing particles of interest are combined with a paramagnetic medium to create a processing solution. The paramagnetic medium comprises a paramagnetic material and a solvent. In accordance with a preferred embodiment, the paramagnetic medium is biocompatible, i.e. capable of being mixed with live cells and not impact the viability of the cells or impacting cellular behavior, e.g. impacting gene expression. The paramagnetic material may be selected from the group comprising gadolinium, titanium, vanadium, dysprosium, chromium, manganese, iron, nickel, gallium, including ions thereof and combinations thereof. In accordance with an embodiment the paramagnetic material is selected from the group comprising titanium (III) ion, gadolinium (III) ion, vanadium (I) ion, nickel (II) ion, chromium (III) ion, vanadium (III) ion, dysprosium (III) ion, cobalt (II) ion, and gallium (III) ion. In accordance with a preferred embodiment, the paramagnetic material comprises a chelated compound. In accordance with a preferred embodiment, the paramagnetic material comprises a gadolinium chelate, a dysprosium chelate, or a manganese chelate. In accordance with an embodiment, the paramagnetic medium comprises a paramagnetic material, salts, and other additives that function to maintain cellular integrity.

In accordance with an embodiment, the paramagnetic material may be present in the paramagnetic medium at a concentration of at least about 10 mM, 20 mM, 30 mM, 40 mM, 50 mM, 60 mM, 70 mM, 80 mM, 90 mM, 100 mM, 120 mM, 150 mM, 200 mM, 250 mM, 300 mM, 500 mM, or 1 M. In accordance with an embodiment, the paramagnetic material may be present in the paramagnetic medium at a concentration of about 10 mM to about 50 mM, about 25 mM to about 75 mM, about 50 mM to about 100 mM, about 100 mM to about 150 mM, about 150 mM to about 200 mM, about 200 mM to about 250 mM, about 250 mM to about 300 mM, about 300 mM to about 500 mM, or about 500 mM to about 1 M.

In accordance with an embodiment, the paramagnetic material comprises gadolinium and is present in the paramagnetic medium at a concentration of at least about 10 mM, 20 mM, 30 mM, 40 mM, 50 mM, 60 mM, 70 mM, 80 mM, 90 mM, or 100 mM. In accordance with an embodiment, the paramagnetic material comprises gadolinium and is present in the paramagnetic medium at a concentration of about 10 mM to about 50 mM, about 25 mM to about 75 mM, or about 50 mM to about 100 mM.

The processing solution is injected into the inlet port of the particle isolation device and flows through a fluidic channel structure and into a processing channel. The processing channel comprises a substantially linear fluidic channel that is flanked with an upper magnetic component and a lower magnetic component. As the processing fluid passes through the fluidic channel within the processing channel, the processing fluid is exposed to an asymmetric magnetic field created by the upper magnetic component and the lower magnetic component. The exact configuration of the magnetic components used in this method is predetermined based on the density of the particles of interest relative to the density of the paramagnetic medium. If the particles of interest are denser than the paramagnetic medium, a magnetic component configuration is selected wherein the magnetic force exerted by the lower magnetic component is greater than the magnetic force exerted by the upper magnetic component. Conversely, if the paramagnetic medium is denser than the particles of interest, a magnetic component configuration is selected wherein the magnetic force exerted by the upper magnetic component is greater than the magnetic force exerted by the lower magnetic component.

As the processing fluid passes through the asymmetric magnetic field within the processing channel, the particles of interest will reach a sustainably similar equilibrium height. In accordance with an embodiment of the method of the present invention, substantially all of the particles of interest contained within the processing fluid will reach an equilibrium height defined as the vertical component of the particle position at which the particle remains stationary in a zero fluid flow velocity condition. The equilibrium height spans a range representing less than 35% of the vertical gap between the upper and lower magnets (see, for example, vertical gap 52 shown in FIG. 6), less than 30% of the vertical gap between the upper and lower magnets, less than 25% of the vertical gap between the upper and lower magnets, less than 20% of the vertical gap between the upper and lower magnets, less than 15% of the vertical gap between the upper and lower magnets, less than 10% of the vertical gap between the upper and lower magnets, less than 8% of the vertical gap between the upper and lower magnets, less than 6% of the vertical gap between the upper and lower magnets, or less than 5% of the vertical gap between the upper and lower magnets. In accordance with an embodiment of the method of the present invention, at least approximately 70%, 75%, 80%, 85%, 90%, or 95% of the particles of interest contained within the processing fluid will reach an equilibrium height that spans a range representing less than 35% of the vertical gap between the upper and lower magnets, less than 30% of the vertical gap between the upper and lower magnets, less than 25% of the vertical gap between the upper and lower magnets, less than 20% of the vertical gap between the upper and lower magnets, less than 15% of the vertical gap between the upper and lower magnets, less than 10% of the vertical gap between the upper and lower magnets, less than 8% of the vertical gap between the upper and lower magnets, less than 6% of the vertical gap between the upper and lower magnets, or less than 5% of the vertical gap between the upper and lower magnets.

The equilibrium height of levitated particles between the magnets can be considered in terms of the proportion of the height from the bottom magnet's upper surface to the top magnet's lower surface. The equilibrium height can be expressed as a percentage of this height, or "relative height", where a relative height of 0% is at the bottom magnet, relative height of 100% is at the top magnet, and 50% is at a height vertically centered between the magnets. In accordance with an embodiment of the present invention, the equilibrium relative height distribution of substantially all the particles of interest contained within the processing fluid will vary by no more than about 35% or about 30% or about 25% or about 20% or about 15% or about 10% or about 5%. In accordance with an embodiment of the present invention, the equilibrium relative height distribution of at least approximately 70%, 75%, 80%, 85%, 90%, or 95% of the particles of interest contained within the processing fluid will vary by no more than about 35% or about 30% or about 25% or about 20% or about 15% or about 10% or about 5%.

Once the particles of interest reach their equilibrium height, they pass through a splitter that geometrically divides the processing solution into multiple fractions. Because the particles of interest are geometrically isolated within the processing solution, substantially all the particles of interest are retained within the effluent of certain geometric fractions. The geometric effluent fraction or fractions containing the particles of interest are then collected and recombined if the particles of interest are present more than one fraction, thereby isolating the particles of interest. In some embodiments it may be necessary to separate the cells from the paramagnetic medium. This may be done through dilution if separation of the cells from the paramagnetic medium is desired.

Alternatively, the division of processing solution into each effluent fraction may be achieved by increasing or decreasing the fluid flow toward individual outlets, such that the ratio of division can be modified. In accordance with an embodiment the ratio may be modified by up to 50%. For example, if the splitter comprises two channels with equal cross section, the geometric ratio of division is 1:1. By withdrawing a larger (or smaller) amount of fluid into one fraction through the application of a larger (or smaller) pumping rate than is applied to the other fraction, the ratio of division can be altered, e.g. to about 3:1, 4:1, 5:1, 6:1, 7:1, 8:1, 9:1 or 10:1. In a preferred embodiment, the division for such geometric ratio would be within the range of about 2:1 to about 1:2.

V. Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, when any range is described herein, unless clearly stated otherwise, that range includes all values therein and all sub-ranges therein.

Also, and more generally, in accordance with disclosures, discussions, examples and embodiments herein, there may be employed conventional fluidics, molecular biology, cellular biology, microbiology, and recombinant DNA techniques within the skill of the art. Such techniques are explained fully in the literature. (See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986.) These published resources are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls as a preferred embodiment, and any contradiction may be viewed as an alternative embodiment. Subject matter in the Examples is incorporated into this section to the extent not already present.

Example

A device in accordance with the present invention was used to separate polymer beads, which simulate particles of interest, such as cells and other particles described hereinabove. The device used in this experiment included an ovoid channel that was 80 mm long and 1.78 mm in height. Neodymium magnets were positioned above and below the channel with the channel resting on the bottom magnet and a separation between the channel and the upper magnet at a vertical distance of approximately 400 microns. The upper magnet was 5 mm tall. The lower magnet was 10 mm tall and included a stack of 2 magnets, each of 5 mm. The bead and gadobutrol mix was pushed into the capillary with a single syringe located on the inlet side of the capillary.

Approximately equal amounts of three groups of polymer beads having three different densities were mixed together. The beads included beads with densities of 1.091 g/cc, 1.014 g/cc and 1.05 g/cc, and approximate corresponding diameters of 35 microns, 35 microns, and 10 microns, respectively. The mixed beads were combined with a 100 mM solution of gadobutrol in 1X phosphate-buffered saline (PBS). The beads/gadobutrol fluid mixture was injected into the device's channel. As the mixture flowed through the channel it was exposed to the magnetic field exerted by the magnets, and the three types of beads responded differently by levitating to different heights.

Figure 23:
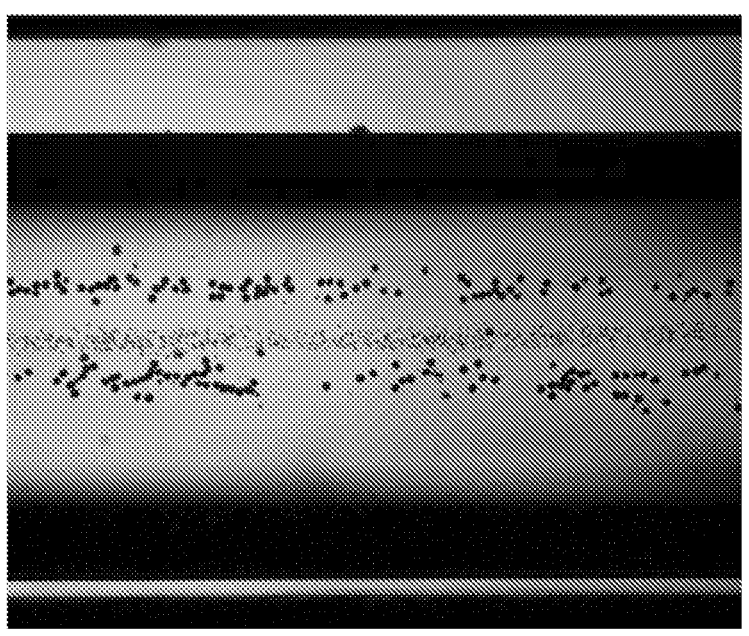
FIG. 23 is a photograph illustrating the isolation of particles in accordance with the present invention.
Figure 24:
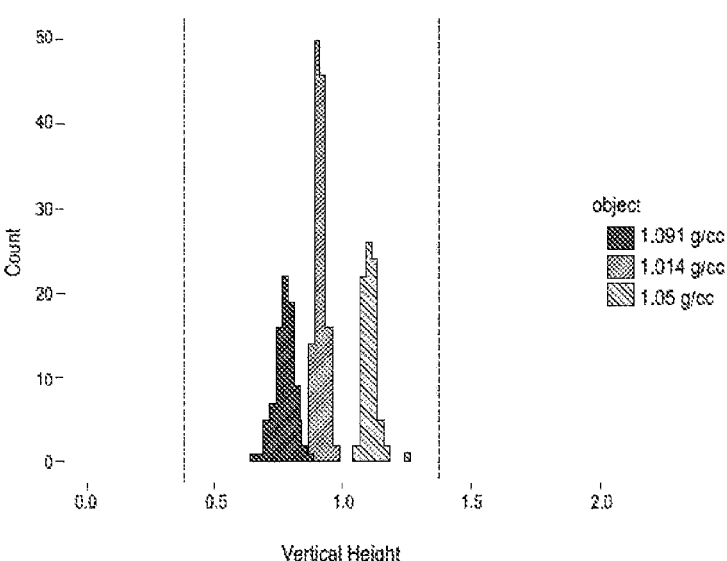
FIG. 24 is graph showing the particle distribution of the isolated particles shown in FIG. 23.

The results are shown in FIG. 23 and FIG. 24. FIG. 23 is an image of the beads as they passed through the magnetic field, and the separation of the three types of beads is clearly visible. FIG. 24 is a graph showing the height distribution of the various beads, and again illustrates the clear separation of the beads.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of separating cells of a first cell type from a heterogeneous population of cells comprising:
   (a) providing a processing solution comprising the heterogeneous population of cells and a paramagnetic medium;
   (b) passing the processing solution through a cell isolation device, wherein the cell isolation device comprises (i) a fluidic channel, wherein the fluidic channel comprises a substantially linear portion, and (ii) an upper magnetic component and a lower magnetic component that are positioned on opposite sides of a substantial portion of the substantially linear portion of the fluidic channel along a substantially vertical axis between the upper magnetic component and the lower magnetic component, and wherein the upper magnetic component and the lower magnetic component create an asymmetric magnetic field within the substantially linear portion of the fluidic channel and along the substantially vertical axis between the upper magnetic component and the lower magnetic component, wherein the upper magnetic component emits a magnetic field that is different from a magnetic field emitted by the lower magnetic component;
   (c) magnetically levitating, by the asymmetric magnetic field, the heterogeneous population of cells within the fluidic channel to cause;
      (i) substantially all of the cells of the first cell type to reach the same first cell-type specific equilibrium height and
      (ii) cells of a different cell type to reach an equilibrium height that is different from the first cell-type specific equilibrium height,
      based at least in part on a difference in magnetic susceptibility between the cells of the first cell type and the cells of the different cell type,
   wherein the first cell-type specific equilibrium height is a vertical position at which magnetic force and corrected gravitational force are sufficiently balanced to cause the cells of the first cell type to remain stationary under conditions of zero fluid flow in the vertical direction,
   thereby separating the cells of the first cell type from the heterogeneous population of cells.

2. The method of claim 1, further comprising observing, analyzing, recording, or collecting the cells of the first cell type.

3. The method of claim 1, wherein the substantially linear portion of the fluidic channel further comprises at least one input port and at least two output ports.

4. The method of claim 3, wherein the at least two output ports comprise a plurality of vertically spaced channels in the substantially linear portion of the fluidic channel.

5. The method of claim 3, wherein the cell isolation device further comprises one or more pumps configured to drive fluid from the at least one input port through the substantially linear portion of the fluidic channel and out at least one output port of the at least two output ports.

6. The method of claim 1,
   wherein substantially all of the heterogeneous population of cells each reaches a respective equilibrium height,
   wherein a difference between a highest equilibrium height of the heterogeneous population of cells and a lowest equilibrium height of the heterogeneous population of cells is less than 35% of a vertical gap between the upper magnetic component and the lower magnetic component.

7. The method of claim 6, wherein an equilibrium height distribution of substantially all of the heterogeneous population of cells is less than 5000 microns.

8. The method of claim 7, wherein the equilibrium height distribution of substantially all of the heterogeneous population of cells is from about 1 micron to about 5000 microns.

9. The method of claim 6, wherein the substantially all the heterogeneous population of cells comprise at least 70% of the heterogeneous population of cells.

10. The method of claim 6, further comprising, after substantially all of the heterogeneous population of cells each reaches a respective equilibrium height, passing the heterogeneous population of cells through a splitter that geometrically divides the processing solution into multiple effluent fractions, wherein one or more effluent fractions of the multiple effluent fractions comprise substantially all of the heterogeneous population of cells collected.

11. The method of claim 10, wherein the heterogeneous population of cells comprises a microorganism, bacteria, or combinations thereof.

12. The method of claim 1, further comprising separating the cells of the first cell type from the paramagnetic medium.

13. The method of claim 11, wherein the paramagnetic medium comprises a paramagnetic material and a solvent.

14. The method of claim 11, wherein the paramagnetic medium comprises a paramagnetic material, salts, and other additives that function to maintain cellular integrity.

15. The method of claim 1, wherein a density of the heterogeneous population of cells is greater than a density of the paramagnetic medium, and wherein a magnetic field emitted by the lower magnetic component is greater than a magnetic field emitted by the upper magnetic component.

16. The method of claim 1, wherein a density of the heterogeneous population of cells is less than a density of the paramagnetic medium, and wherein a magnetic field emitted by the lower magnetic component is less than a magnetic field emitted by the upper magnetic component.

17. The method of claim 1, wherein the upper magnetic component emits a greater magnetic field than the magnetic field created by the lower magnetic component.

18. The method of claim 1, wherein the upper magnetic component emits a smaller magnetic field than the magnetic field created by the lower magnetic component.

*   *   *   *   *